(12) United States Patent
Nagao

(10) Patent No.: US 8,901,353 B2
(45) Date of Patent: Dec. 2, 2014

(54) POLYIMIDE PRECURSOR, POLYIMIDE, AND LIQUID CRYSTAL ALIGNING AGENT

(75) Inventor: Masato Nagao, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 168 days.

(21) Appl. No.: 13/255,644

(22) PCT Filed: Mar. 9, 2010

(86) PCT No.: PCT/JP2010/053913
§ 371 (c)(1),
(2), (4) Date: Nov. 21, 2011

(87) PCT Pub. No.: WO2010/104082
PCT Pub. Date: Sep. 16, 2010

(65) Prior Publication Data
US 2012/0088888 A1     Apr. 12, 2012

(30) Foreign Application Priority Data

Mar. 10, 2009   (JP) ................. 2009-056426

(51) Int. Cl.
| | |
|---|---|
| C07C 211/00 | (2006.01) |
| C08G 73/10 | (2006.01) |
| C07C 229/18 | (2006.01) |
| C09D 179/08 | (2006.01) |
| C07C 271/22 | (2006.01) |
| G02F 1/1337 | (2006.01) |

(52) U.S. Cl.
CPC ...... *C08G 73/1078* (2013.01); *G02F 1/133723* (2013.01); *C07C 229/18* (2013.01); *C09D 179/08* (2013.01); *C07C 271/22* (2013.01)
USPC .......................................................... 564/305

(58) Field of Classification Search
CPC .......................... C08G 73/1078; C07C 271/22
See application file for complete search history.

(56) References Cited

U.S. PATENT DOCUMENTS 4,095,028 A      6/1978  Hall et al.
5,457,180 A  *  10/1995  Zacharie ................. 530/333
(Continued)

FOREIGN PATENT DOCUMENTS

| JP | 8 54631 | 2/1996 |
|---|---|---|
| JP | 2001 89426 | 4/2001 |

(Continued)

OTHER PUBLICATIONS

Manabe, N., et al., "Residual DC Voltage Measurement Utilizing Capacitor's Dielectric Absorption Method," Proceedings of the 22$^{nd}$ Japanese Liquid Crystal Society Annual Meeting, pp. 365-366, (Sep. 30, 1996) (with English abstract).

(Continued)

*Primary Examiner* — Clinton Brooks
(74) *Attorney, Agent, or Firm* — Oblon, Spivak, McClelland, Maier & Neustadt, L.L.P.

(57) ABSTRACT

To provide a novel diamine which is useful as the starting material of a novel polyimide precursor or polyimide which can provide a liquid crystal alignment film having a low volume resistivity, a liquid crystal aligning agent containing these polymers, and a liquid crystal alignment film. The novel diamine is a compound represented by any one of the following formulae (A) to (C):

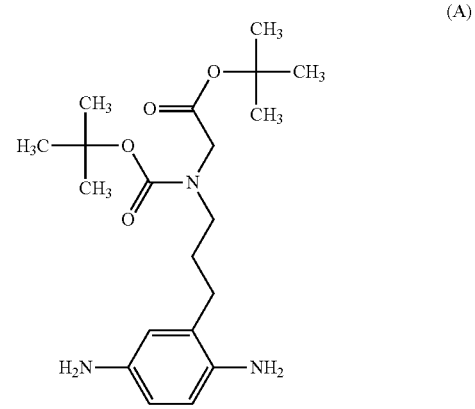

(A)

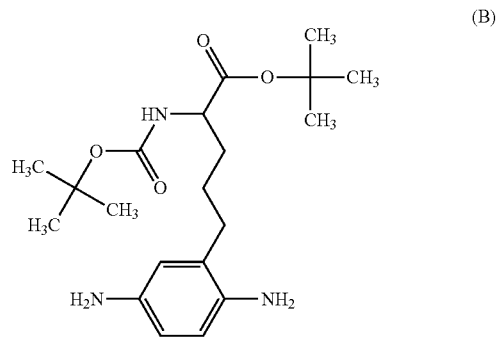

(B)

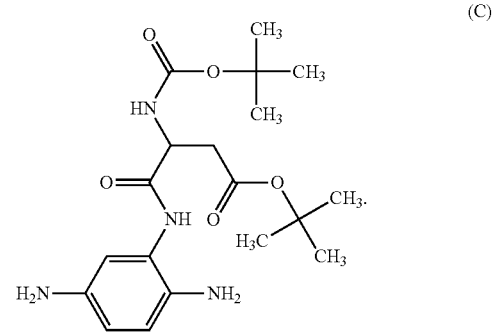

(C)

1 Claim, No Drawings

(56) References Cited

U.S. PATENT DOCUMENTS

| | | | |
|---|---|---|---|
| 7,670,784 B2 * | 3/2010 | Shimamoto | 435/7.1 |
| 2006/0021159 A1 | 2/2006 | Sabelle et al. | |
| 2008/0070321 A1 | 3/2008 | Shimamoto | |
| 2010/0069941 A1 | 3/2010 | Cohen et al. | |

FOREIGN PATENT DOCUMENTS

| | | | | |
|---|---|---|---|---|
| JP | 2005 239727 | | 9/2005 | |
| JP | 2007 94317 | | 4/2007 | |
| JP | 2007 241249 | | 9/2007 | |
| JP | 2008 203332 | | 9/2008 | |
| WO | 2006 070737 | | 7/2006 | |
| WO | WO2008038841 | * | 4/2008 | C07D 285/13 |
| WO | 2010 050523 | | 5/2010 | |

OTHER PUBLICATIONS

Nakanowatari, J., et al., "Effect of the Thickness of Alignment Layer on the Low-Frequency Dielectric Dispersion of a Nematic Liquid Crystal," Japanese Journal of Applied Physics, vol. 35, No. 1B, pp. L111-L113, (Jan. 15, 1996).

Liang, T., et al., "Charge-discharge Characteristics of Thin Polymer Films Used for Liquid Crystal Alignment Materials," Proceedings of the 23$^{rd}$ Japanese Liquid Crystal Society Annual Meeting, pp. 138-139, (Sep. 24, 1997) (with English abstract).

International Search Report Issued Jun. 15, 2010 in PCT/JP10/053913 Filed Mar. 9, 2010.

Office Action issued Jun. 26, 2014, in Taiwan Patent Application No. 099106924, filed Mar. 10, 2010.

* cited by examiner

POLYIMIDE PRECURSOR, POLYIMIDE, AND LIQUID CRYSTAL ALIGNING AGENT

TECHNICAL FIELD

The present invention relates to a novel polyimide precursor or polyimide useful for a liquid crystal alignment film of a liquid crystal display element, and a liquid crystal aligning agent comprising such a polymer. Further, the present invention also relates to a novel diamine which can be used for obtaining such a polymer.

BACKGROUND ART

In the liquid crystal display element, a charge accumulated in the element at the time of driving has been known to cause an image sticking phenomenon, and the amount of such a charge accumulation has been known to be affected by the physical properties such as the volume resistivity, relative dielectric constant, etc. of components constituting the liquid crystal display element, such as liquid crystal, a liquid crystal alignment film, electrodes, an insulating film or a color filter (Non-Patent Document 1, Non-Patent Document 2 and Non-Patent Document 3).

The liquid crystal alignment film to be used for the liquid crystal display element is mainly produced by applying and baking a varnish of a polyamic acid, a polyamic acid ester or a polyimide. Further, with regard to the liquid crystal alignment film, a method of reducing the occurrence of an image sticking phenomenon of liquid crystal display element by lowering its volume resistivity has been proposed (Patent Document 1 and Patent Document 2).

PRIOR ART DOCUMENTS

Patent Documents

Patent Document 1: JP-A-8-54631
Patent Document 2: JP-A-2007-241249

Non-Patent Documents

Non-Patent Document 1: Proceedings of the 22nd Japanese Liquid Crystal Society Annual Meeting, p. 365-366
Non-Patent Document 2: Jpn. J. Appl. Phys. 1996, Vol. 35, L111-L113
Non-Patent Document 3: Proceedings of the 23rd Japanese Liquid Crystal Society Annual Meeting, p. 138-139

DISCLOSURE OF INVENTION

Technical Problem

It is an object of the present invention to provide a novel polyimide precursor or polyimide which can give a liquid crystal alignment film having a low volume resistivity. Further, it is another object of the present invention to provide a liquid crystal alignment film having an excellent image sticking property, and a liquid crystal aligning agent to be used for obtaining the liquid crystal alignment film. Further, another object is to provide a novel diamine useful as a starting material for these polymers.

Solution to Problem

The presenters have conducted extensive study to accomplish the above objects and as a result, have arrived at the present invention. The present invention provides the followings.

1. A polyimide precursor having polymerized units represented by the following formula (1), and characterized by satisfying any one of the following (i) to (iii);

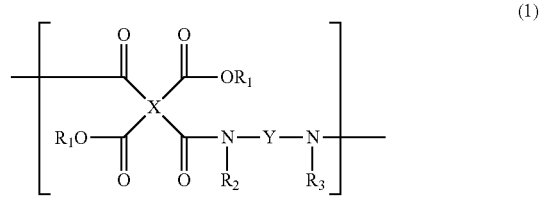

wherein $R_1$ is a hydrogen atom or a $C_{1-4}$ alkyl group, each of $R_2$ and $R_3$ which are independent of each other is a hydrogen atom or a monovalent organic group, X is a tetravalent organic group, and Y is a bivalent organic group;

(i) the structure of X, Y or each of them in formula (1) has a group represented by the following formula (2);

(ii) $R_2$, $R_3$ or each of them in formula (1) is a group represented by the following formula (2);

(iii) the structure of X, Y or each of them in formula (1) has a group represented by the following formula (2), and $R_2$, $R_3$ or each of them is a group represented by following formula (2):

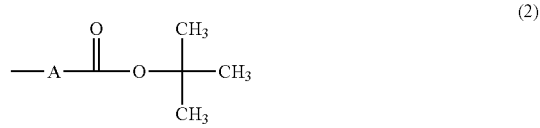

wherein A is a single bond or a bivalent organic group, provided that an atom to which the t-butoxycarbonyl group in formula (2) is bonded is a carbon atom.

2. The polyimide precursor according to the above 1, wherein the structure of Y in formula (1) has a group represented by formula (2).

3. The polyimide precursor according to the above 1, wherein $R_2$, $R_3$ or each of them in formula (1) is a group represented by formula (2).

4. The polyimide precursor according to the above 2 or 3, wherein Y in formula (1) is a group represented by the following formula (3):

wherein $R_4$ is a single bond or a $C_{1-20}$ bivalent organic group, $R_5$ is a structure represented by formula (2), and a is an integer of from 0 to 4.

5. The polyimide precursor according to the above 4, wherein $R_4$ is a single bond.

6. A polyimide obtained by imidation of the polyimide precursor as defined in any one of the above 1 to 5.

7. A liquid crystal aligning agent comprising the polyimide precursor as defined in any one of the above 1 to 5, and/or the polyimide as defined in the above 6.

8. A liquid crystal alignment film obtained by using the liquid crystal aligning agent as defined in the above 7.

9. A liquid crystal display element having the liquid crystal alignment film as defined in the above 8.

10. A diamine compound represented by the following formula (4):

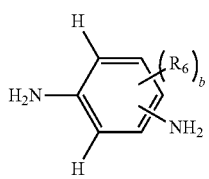
(4)

wherein $R_6$ is a structure represented by the following formula (2), and b is 1 or 2;

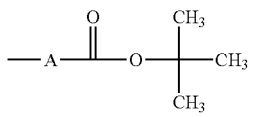
(2)

wherein A is a single bond or a bivalent organic group, provided that an atom to which the t-butoxycarbonyl group is bonded is a carbon atom.

11. A diamine compound represented by the following formula (5):

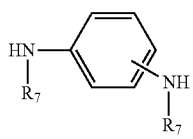
(5)

wherein $R_7$ is a structure represented by the following formula (2):

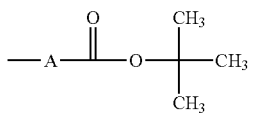
(2)

wherein A is a bivalent organic group, provided that an atom to which the t-butoxycarbonyl group is bonded is a carbon atom.

12. The diamine compound according to the above 10, which is represented by any one of the following formulae (A) to (C).

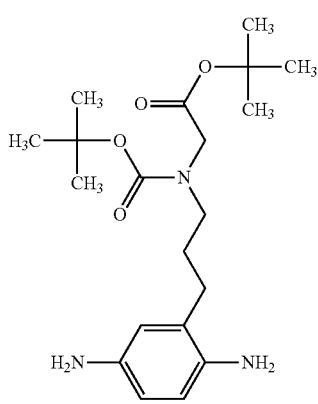
(A)

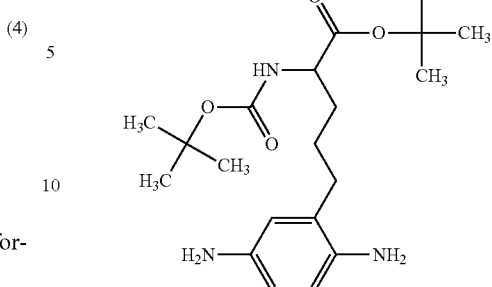
(B)

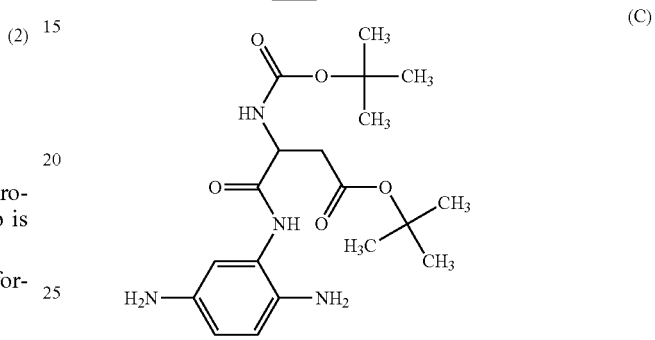
(C)

13. The diamine compound according to the above 11, which is represented by the following formula (D).

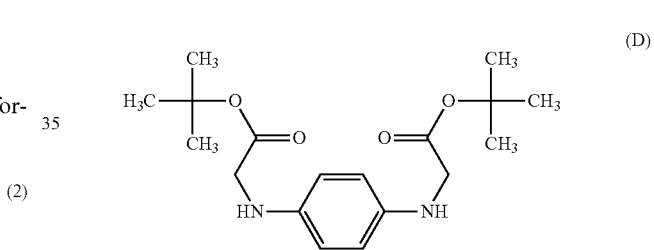
(D)

Advantageous Effects of Invention

The polyimide precursor and polyimide of the present invention provide a polyimide film having a low volume resistivity. The liquid crystal alignment film of the present invention has an excellent image sticking property when it is formed into a liquid crystal display element. The liquid crystal aligning agent of the present invention retains a high storage stability even in a case where various additives are added thereto. The diamine compound of the present invention is reacted with a tetracarboxylic acid derivative, to provide a polyimide precursor or polyimide having a t-butyl ester site, and as a result, a polyimide film obtained from these polymers has a low volume resistivity.

DESCRIPTION OF EMBODIMENTS

The polyimide precursor of the present invention is a polyimide precursor having polymerized units represented by formula (1), and characterized by satisfying any one of the following (i) to (iii), as described above.

In formula (1), $R_1$ is a hydrogen atom or a $C_{1-4}$ alkyl group. As specific examples of the alkyl group, a methyl group, an ethyl group, a propyl group, a 2-propyl group, a butyl group and a t-butyl group may be mentioned. Usually, a polyamic acid ester tends to have a high temperature for imidation as the number of carbon atoms increases in the order of a methyl group, an ethyl group and a propyl group. Accordingly, from the viewpoint of the efficiency for imidation by heat, a methyl group or an ethyl group is preferred, and a methyl group is particularly preferred.

In formula (1), each of $R_2$ and $R_3$ is a hydrogen atom or a monovalent organic group. When $R_2$ or $R_3$ is a monovalent organic group, imidation does not occur at such a site, whereby it becomes possible to control the maximum imidation ratio of a polyimide precursor during imidation by controlling its proportion. For an application for a liquid crystal alignment film, since alignment properties of liquid crystal decrease if the imidation ratio of a polyimide is too low, the proportion that each of $R_2$ and $R_3$ is a hydrogen atom is preferably at least 50%, particularly preferably at least 75%, based on the total amount of a polyimide precursor. As specific examples of the monovalent organic group for $R_2$ or $R_3$, an alkyl group such as a methyl group, an ethyl group, a propyl group, a butyl group, a t-butyl group, a hexyl group, an octyl group or a decyl group; a cycloalkyl group such as a cyclopentyl group or a cyclohexyl group; a bicycloalkyl group such as a bicyclohexyl group; an alkenyl group such as a vinyl group, a 1-propenyl group, a 2-propenyl group, an isopropenyl group, a 1-methyl-2-w propenyl group, a 1-, 2- or 3-butenyl group or a hexenyl group; an aryl group such as a phenyl group, a xylyl group, a tolyl group, a biphenyl group or a naphthyl group; or an aralkyl group such as a benzyl group, a phenylethyl group or a phenylcyclohexyl group, and a group represented by formula (2), may be mentioned. Simply for the purpose of controlling only the maximum imidation ratio, a group having a less adverse effect on the liquid crystal alignment properties such as a methyl group or an ethyl group is preferred, and a methyl group is particularly preferred.

The group represented by the above formula (2) is characterized by having a t-butyl ester structure. Such a t-butyl ester is converted to a carboxy group by heating at a temperature of at least 150° C. Accordingly, the coating liquid containing the polyimide precursor or polyimide of the present invention generates a carboxy group by conducting a heating step at the time of forming a film at a temperature of at least 150° C., whereby the volume resistivity of a formed coating film decreases due to the effect of the carboxy group. When the coating film is used for a liquid crystal alignment film application, the image sticking property of the liquid crystal display element improves by the effect of such a decrease in the volume resistivity.

The polyimide precursor containing a carboxy group can be prepared even when a hydrogen atom is only found in $R_1$ of the above formula (1). However, such a carboxy group is consumed when the polyimide precursor is converted to a polyimide, and then converted to a substructure constituting an imide group, and as a results, it cannot contribute to the decrease in the volume resistivity. Further, if $R_1$ is a t-butyl group, this portion also has a t-butyl ester structure and then generates a carboxy group during a heating step. However, the carboxy group is also consumed in the step of converting the precursor into a polyimide as described above. On the other hand, when a group represented by formula (2) is contained in a condition satisfying any one of the above (i) to (iii), there is a feature such that a carboxy group generated from the structure of formula (2) is retained even after completion of the conversion into a polyimide. However, depending upon a relative position of a t-butoxycarbonyl group shown in formula (2) and an amide group in the main chain of a polyimide precursor, there is a possibility that a stable 5-membered or 6-membered imide ring is formed and then the generated carboxy group is consumed. To eliminate such a possibility, the relative position of the above amide group and t-butoxycarbonyl group is preferably a position by which the number of atoms in between the nitrogen atom of an amide group and the carbon atom of a carbonyl group neighboring a t-butoxy group becomes at most 2 or at least 5, or by which at least one double bond having a trans configuration or at least one triple bond exists in between them.

Further, in a case where a polyimide precursor is imidated in a solution state, an imidation reagent such as a basic compound or an acid anhydride is widely used. However, preparing a polyimide while retaining a carboxy group is difficult since a carboxy group in the polyimide precursor reacts with such an imidation reagent. The t-butyl ester structure of formula (2) does not react with the imidation reagent even at the imidation reaction step, whereby it is possible to obtain a polyimide having a carboxy group by carrying out a heating step thereafter.

Further, in a case where a bifunctional compound which can react with a carboxy group such as an aliphatic diamine or a diepoxy compound is added as an additive to a coating liquid containing a polyimide, gelation of the coating liquid or precipitation of polymers occurs when a carboxy group exists in a polyimide structure, and therefore the coating liquid may not be stored stably for a long period of time. However, such a problem does not occur when a t-butyl ester structure is contained like the structure of formula (2), such being advantageous.

In formula (2), A is a single bond or a bivalent organic group, and is preferably a bivalent organic group represented by the following formula (6) to suppress the decrease in the reactivity of a diamine or to reduce consumption of a carboxy group caused by the above-described reaction with an amide group.

$$-B_1-R_8-B_2-R_9-\qquad(6)$$

(In formula (6), each of $B_1$ and $B_2$ which are independent of each other is a single bond or a bivalent linking group, provided that either one of $B_1$ and $B_2$ is a bivalent linking group. Each of $R_8$ and $R_9$ which are independent of each other is a single bond or a $C_{1-20}$ bivalent hydrocarbon, provided that an atom to which the t-butoxycarbonyl group in formula (2) is bonded is a carbon atom in $B_1$, $B_2$, $R_8$ and $R_9$.)

The specific examples of the above $B_1$ and $B_2$ are shown below, but they are not limited thereto. To improve mechanical properties of the liquid crystal alignment film, at least one of $B_1$ and $B_2$ is preferably B-9.

(B-1)

(B-2)

(B-3)

(B-4)

(B-5)

(B-6)

-continued

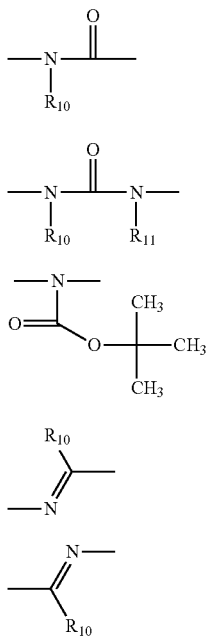

In the above B-5 to B-8, B-10 and B-11, each of $R_{10}$ and $R_{11}$ is a hydrogen atom or a $C_{1-20}$ monovalent hydrocarbon. Here, the monovalent hydrocarbon may, for example, be an alkyl group such as a methyl group, an ethyl group, a propyl group, a butyl group, a t-butyl group, a hexyl group, an octyl group or a decyl group; a cycloalkyl group such as a cyclopentyl group or a cyclohexyl group; a bicycloalkyl group such as a bicyclohexyl group; an alkenyl group such as a vinyl group, a 1-propenyl group, a 2-propenyl group, an isopropenyl group, a 1-methyl-2-propenyl group, a 1-, 2- or 3-butenyl group or a hexenyl group; an aryl group such as a phenyl group, a xylyl group, a tolyl group, a biphenyl group or a naphthyl group; or an aralkyl group such as a benzyl group, a phenylethyl group or a phenylcyclohexyl group.

Further, some or all of hydrogen atoms in such a monovalent hydrocarbon group may be substituted by e.g. a halogen atom, a hydroxy group, a thiol group, an amino group, a phosphoric acid ester group, an ester group, a carboxy group, a phosphate group, a thioester group, an amide group, a nitro group, an organooxy group, an organosilyl group, an organothio group, an organoamino group, a carbamic acid ester group, an acyl group, an alkyl group, a cycloalkyl group, a bicycloalkyl group, an alkenyl group, an aryl group or an aralkyl group. Further, they may have a ring structure.

If $R_{10}$ and $R_{11}$ have a bulky structure such as an aromatic ring or an alicyclic structure, the liquid crystal alignment property decreases, whereby the solubility of polymers may be decreased. Therefore, they are preferably a hydrogen atom or an alkyl group such as a methyl group, an ethyl group, a propyl group or a butyl group, more preferably a hydrogen atom. Further, to improve mechanical properties of the liquid crystal alignment film, they are preferably a carbamic acid t-butyl ester group.

In formula (6), when each of $R_8$ and $R_9$ is a $C_{1-20}$ bivalent hydrocarbon, their specific examples may be mentioned as follows, but they are not limited thereto. An alkylene group such as a methylene group, a 1,1-ethylene group, a 1,2-ethylene group, a 1,1-propylene group, a 1,2-propylene group, a 1,3-propylene group, a 1,2-butylene group, a 1,4-butylene group, a 2,3-butylene group, a 1,6-hexylene group, a 1,8-octylene group or a 1,10-decylene group; a cycloalkylene group such as a 1,2-cyclopropylene group, a 1,2-cyclobutylene group, a 1,3-cyclobutylene group, a 1,2-cyclopentylene group, a 1,1-cyclohexylene group, a 1,2-cyclohexylene group or a 1,4-cyclohexylene group; an alkenylene group such as a 1,1-ethenylene group, a 1,2-ethenylene group, a 1,2-ethenylenemethylene group, a 1-methyl-1,2-ethenylene group, a 1,2-ethenylene-1,1-ethylene group, a 1,2-ethenylene-1,2-ethylene group, a 1,2-ethenylene-1,2-propylene group, a 1,2-ethenylene-1,3-propylene group, a 1,2-ethenylene-1,4-butylene group, a 1,2-ethenylene-1,2-butylene group, a 1,2-ethenylene-1,2-heptylene group or a 1,2-ethenylene-1,2-decylene group; an alkynylene group such as an ethynylene group, an ethynylenemethylene group, an ethynylene-1,1-ethylene group, an ethynylene-1,2-ethylene group, an ethynylene-1,2-propylene group, an ethynylene-1,3-propylene group, an ethynylene-1,4-butylene group, an ethynylene-1,2-butylene group, an ethynylene-1,2-heptylene group or an ethynylene-1,2-decylene group; an arylene group such as a 1,2-phenylene group, a 1,3-phenylene group, a 1,4-phenylene group, a 1,2-naphthylene group, a 1,4-naphthylene group, a 1,5-naphthylene group, a 2,3-naphthylene group, a 2,6-naphthylene group, a 3-phenyl-1,2-phenylene group, a 2,2'-diphenylene group or a 2,2'-dinaphtho-1,1'-yl group; and a bifunctional hydrocarbon group comprised of an arylene group and an alkylene group such as a 1,2-phenylenemethylene group, a 1,3-phenylenemethylene group, a 1,4-phenylenemethylene group, a 1,2-phenylene-1,1-ethylene group, a 1,2-phenylene-1,2-ethylene group, a 1,2-phenylene-1,2-propylene group, a 1,2-phenylene-1,3-propylene group, a 1,2-phenylene-1,4-butylene group, a 1,2-phenylene-1,2-butylene group, a 1,2-phenylene-1,2-hexylene group, a methylene-1,2-phenylenemethylene group, a methylene-1,3-phenylenemethylene group or a methylene-1,4-phenylenemethylene group may be mentioned.

Further, some or all of hydrogen atoms in such a bivalent hydrocarbon group may be substituted by e.g. a halogen atom, a hydroxy group, a thiol group, an amino group, a phosphoric acid ester group, an ester group, a carboxy group, a phosphate group, a thioester group, an amide group, a nitro group, an organooxy group, an organosilyl group, an organothio group, an organoamino group, a carbamic acid ester group, an acyl group, an alkyl group, a cycloalkyl group, a bicycloalkyl group, an alkenyl group, an aryl group or an aralkyl group. Further, to improve mechanical properties of the liquid crystal alignment film, a carbamic acid t-butyl ester group is preferred.

Each of $R_8$ and $R_9$ is preferably a $C_{1-5}$ alkylene group, a $C_{1-5}$ alkenylene group or a $C_{1-5}$ alkynylene group, since the liquid crystal alignment properties improve when they have a small number of carbon atoms. Further, each of $R_{10}$ and $R_{11}$, or either one of them is preferably a single bond.

Here, specific and preferred examples of the structure represented by formula (2) are shown below, but the present invention is by no means limited thereto.

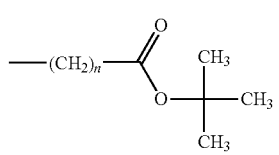

$n = 1\sim20$ (8)
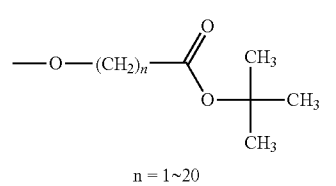
n = 1~20
(9)
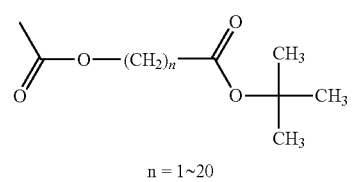
n = 1~20
(10)
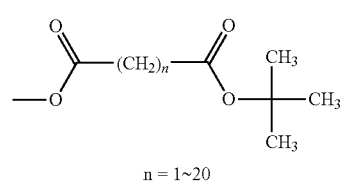
n = 1~20
(11)
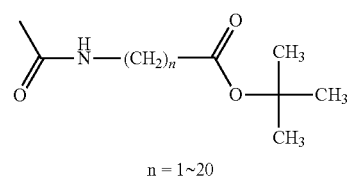
n = 1~20
(12)
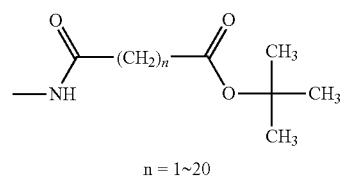
n = 1~20
(13)
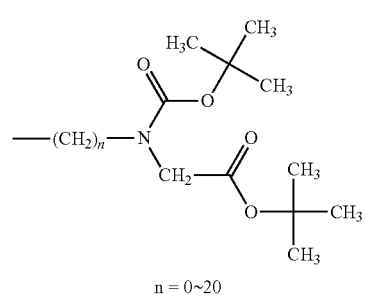
n = 0~20
(14)
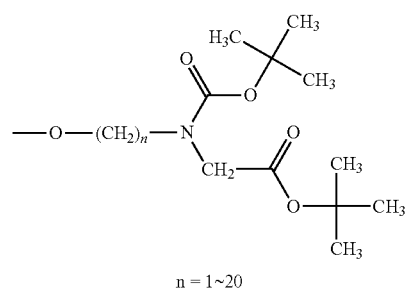
n = 1~20
(15)
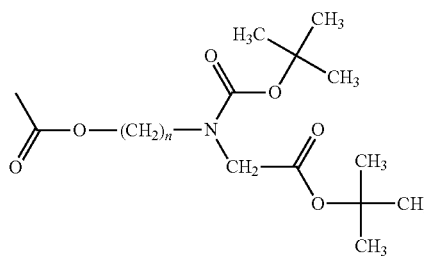
n = 1~20
(16)
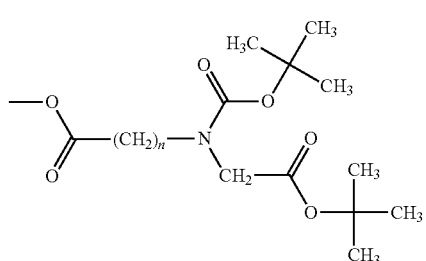
n = 1~20
(17)
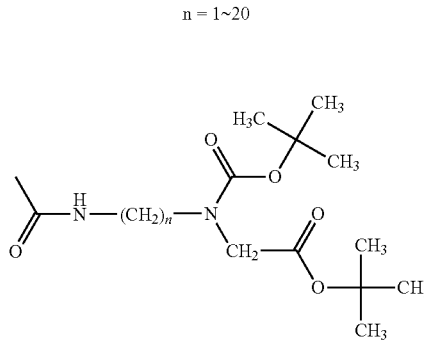
n = 1~20
(18)
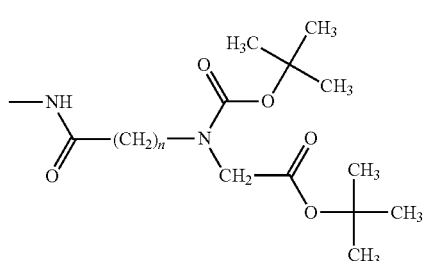
n = 1~20
(19)
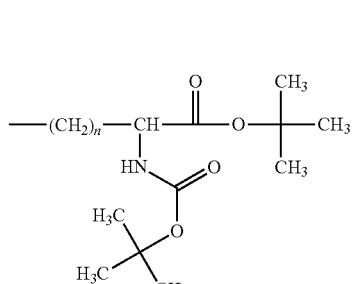
n = 0-20

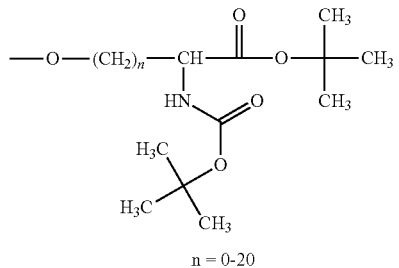

(20)

n = 0-20

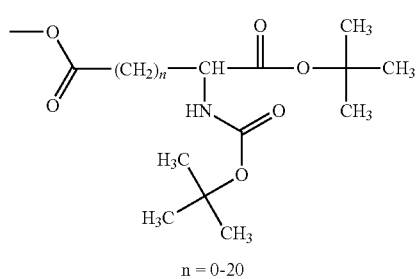

(21)

n = 0-20

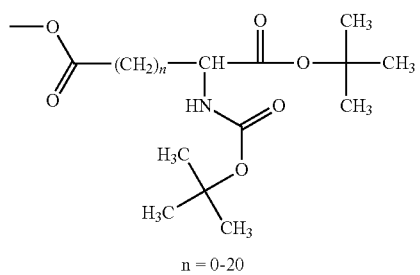

(21)

n = 0-20

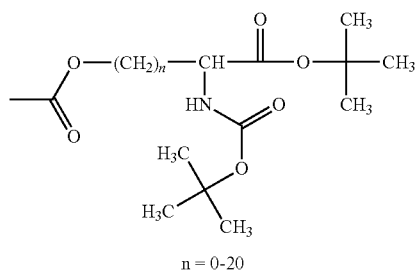

(22)

n = 0-20

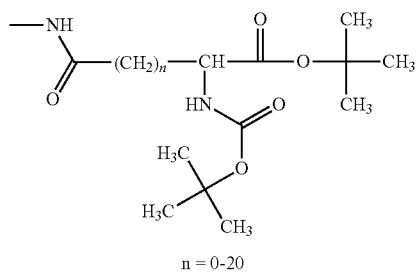

(23)

n = 0-20

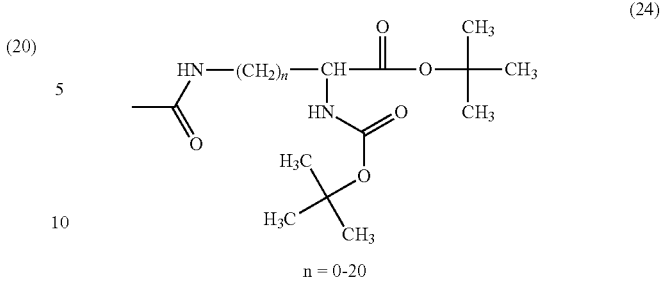

(24)

n = 0-20

In the above formulae (7) to (24), it is preferred that n is selected based on their basic structures so that the number of atoms present in a route in the main chain between the nitrogen atom of an amide group and the carbon atom of a carbonyl group neighboring a t-butoxy group becomes at most 2 or at least 5, to eliminate the possibility of reaction between the above-described amide group in the main chain and a carboxy group generated from the structure of formula (2). Further, since the liquid crystal alignment properties improve when the number of carbon atoms is small, n is preferably from 0 to 10, more preferably from 0 to 5.

In the polymerized units comprising the polyimide precursor of the present invention, the position where a group represented by formula (2) exists may be any one of X, Y, $R_2$ and $R_3$ in formula (1). Among them, a form wherein the structure of Y in formula (1) has a group represented by formula (2), and a form wherein $R_2$, $R_3$ or each of them in formula (1) is a group represented by formula (2), are preferred from the viewpoint of the simplicity of preparation of a monomer to be used as a starting material of the polyimide precursor and the handling efficiency of the monomer.

Further, when $R_2$ or $R_3$ in formula (1) is a group represented by formula (2), imidation of an amide group to which formula (2) is bonded does not occur, whereby it becomes possible to control the maximum imidation ratio at the time of imidating the polyimide precursor by controlling such a proportion. On the contrary, when imidation of the polyimide precursor is not required to be inhibited, a form wherein each of $R_2$ and $R_3$ in formula (1) is a hydrogen atom, and X, Y or each of them in formula (1) is a group represented by formula (2) may be selected. In a case where a polyimide is used as a liquid crystal alignment film, since the alignment properties of liquid crystal decrease if the imidation ratio of a polyimide is too low, the proportion that each of $R_2$ and $R_3$ is a hydrogen atom is preferably at least 50%, particularly preferably at least 75%, based on the total amount of the polyimide precursor.

The polyimide precursor of the present invention may have polymerized units which can be represented by formula (1) and have no group represented by formula (2) in any one of X, Y, $R_2$ and $R_3$. In such a case, for the purpose of reducing the volume resistivity of a polyimide, the content ratio of formula (2) which exists in any one of X, Y, $R_2$ and $R_3$ is preferably at least 0.05, particularly preferably at least 0.10, based on the polymerized units represented by formula (1).

Based on the above definition, e.g. in a case where polymerized units represented by formula (1) contained in the polyimide precursor are only "polymerized units wherein each of X and Y in formula (1) has one group represented by formula (2), and each of $R_2$ and $R_3$ is a group represented by formula (2)", the content ratio of formula (2) in the polyimide precursor is 4.00.

In the above formula (1), X is a tetravalent organic group, and is not particularly limited. In the polyimide precursor, X may have two or more types of structures in combination. Specific examples of X are as follows. The following structures X-1 to X-46 may be mentioned as structures having no group represented by formula (2). Further, as structures having a group represented by formula (2), ones in which at least one hydrogen atom optionally selected in the structures X-1 to X-46 is substituted by a group represented by formula (2) may be mentioned. Further, from the viewpoint of the availability of monomers, the number of a group represented by formula (2) in X is preferably at most 4.

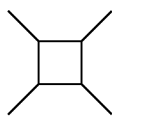
(X-1)

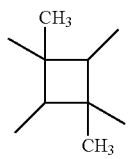
(X-2)

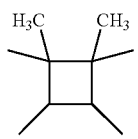
(X-3)

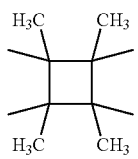
(X-4)

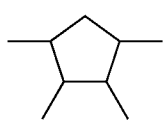
(X-5)

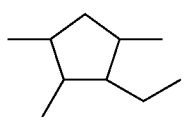
(X-6)

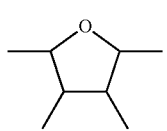
(X-7)

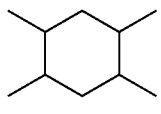
(X-8)

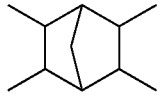
(X-9)

-continued

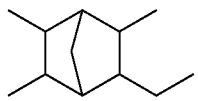
(X-10)

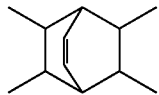
(X-11)

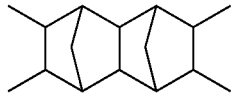
(X-12)

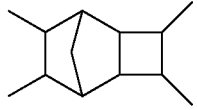
(X-13)

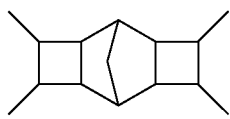
(X-14)

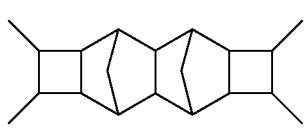
(X-15)

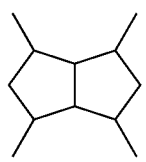
(X-16)

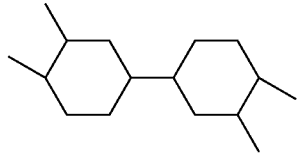
(X-17)

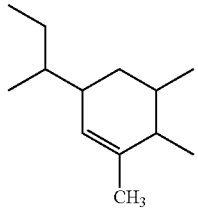
(X-18)

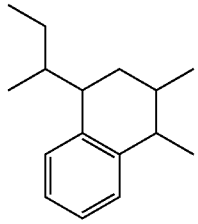
(X-19)

(X-20)
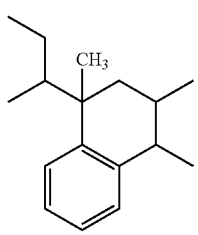
(X-21)
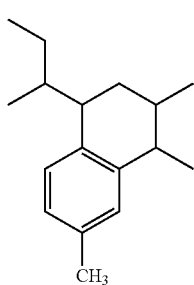
(X-22)
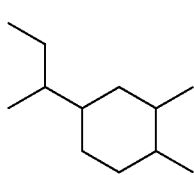
(X-23)
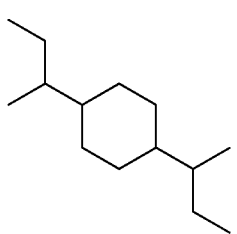
(X-24)
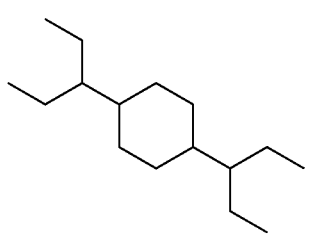
(X-25)
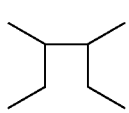
(X-26)
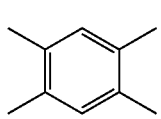
(X-27)
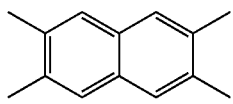
(X-28)
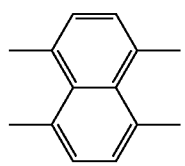
(X-29)
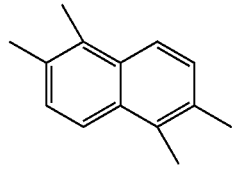
(X-30)
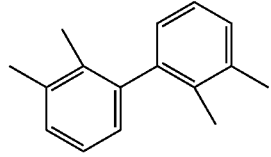
(X-31)
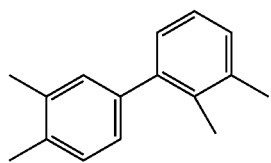
(X-32)
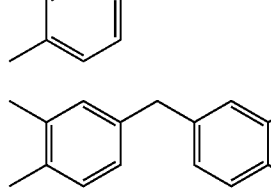
(X-33)
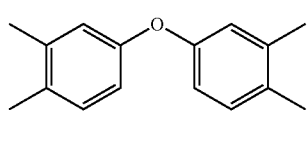
(X-34)
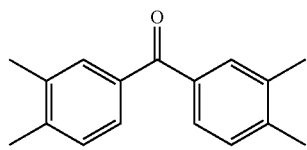
(X-35)
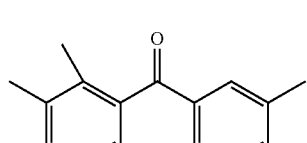
(X-36)
(X-37)

(X-38) 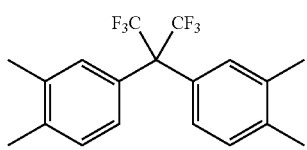

(X-39) 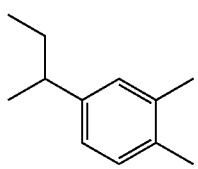

(X-40) 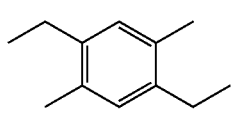

(X-41) 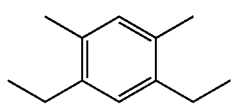

(X-42) 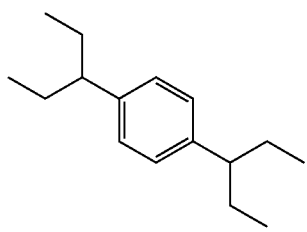

(X-43) 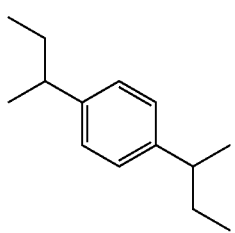

(X-44) 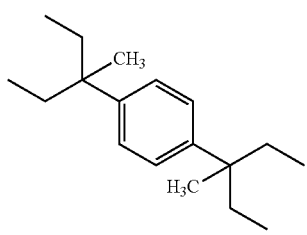

(X-45) 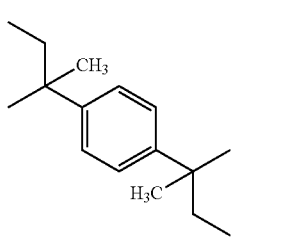

(X-46) 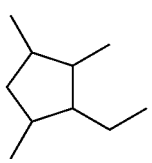

In the above formula (1), Y is a bivalent organic group, and is not particularly limited. In the polyimide precursor, Y may have two or more types of structures in combination. Specific examples of Y are as follows. The following structures Y-1 to Y-97 may be mentioned as structures having no group represented by formula (2). Further, as structures having a group represented by formula (2), ones in which at least one hydrogen atom optionally selected in the structures Y-1 to X-97 is substituted by a group represented by formula (2) may be mentioned. Further, from the viewpoint of the availability of monomers, the number of a group represented by formula (2) in Y is preferably at most 4.

(Y-1) 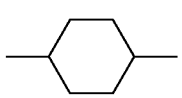

(Y-2) 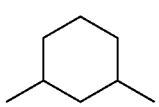

(Y-3) 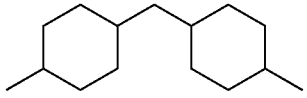

(Y-4) 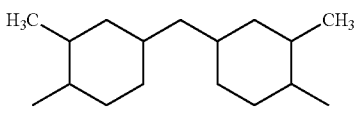

(Y-5) 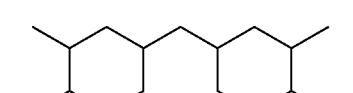

(Y-6) 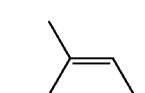

(Y-7) 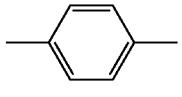

(Y-8) 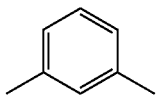

(Y-9) 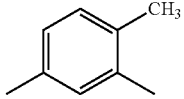

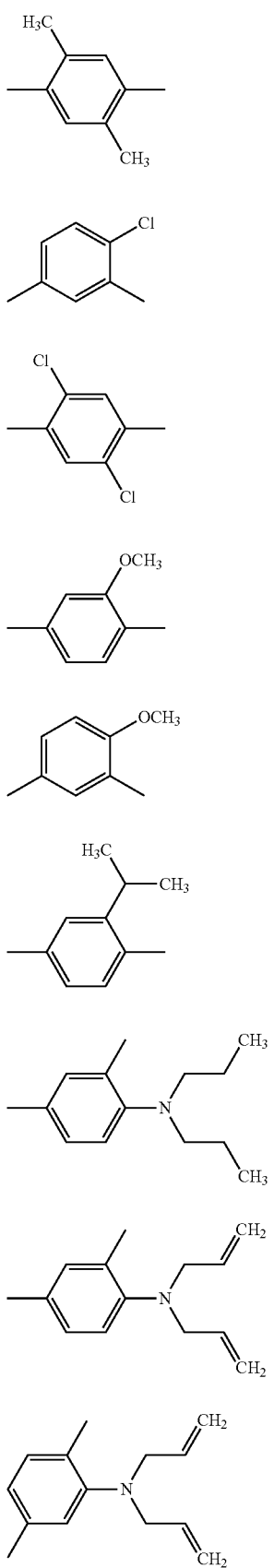
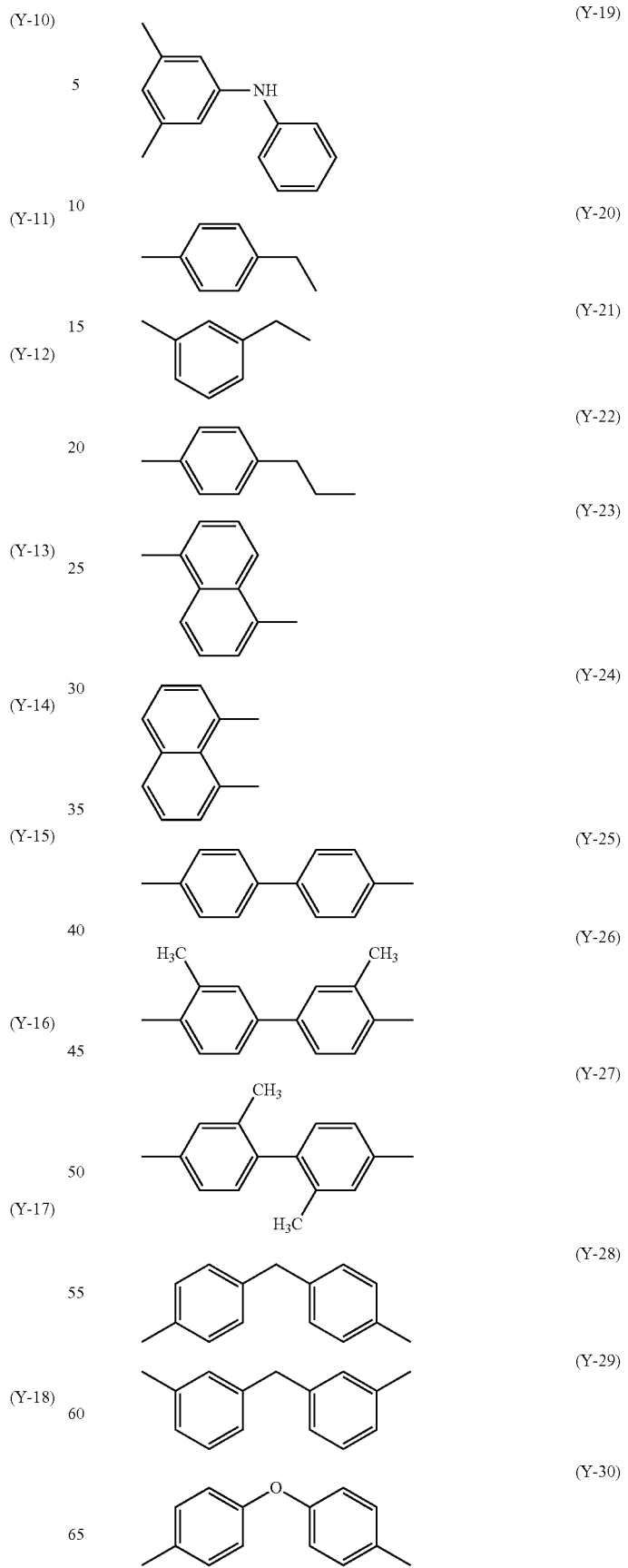

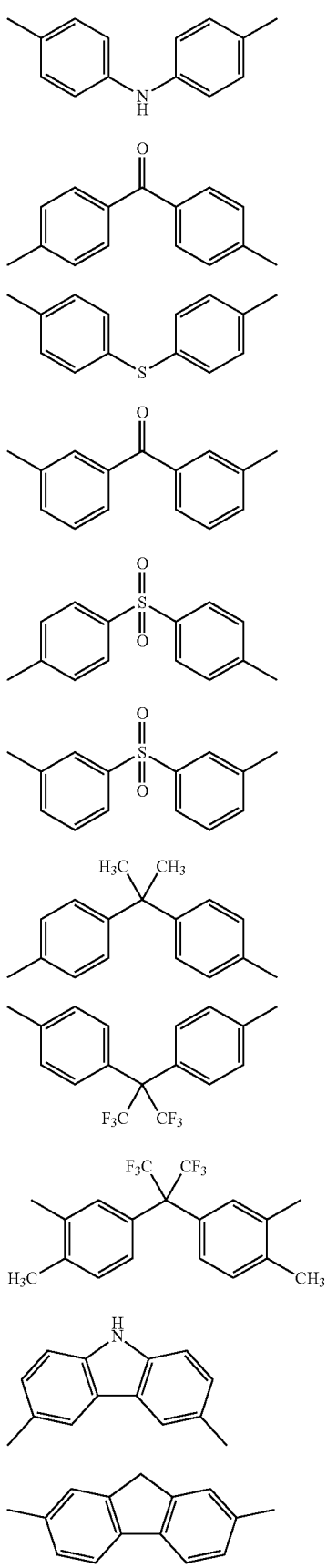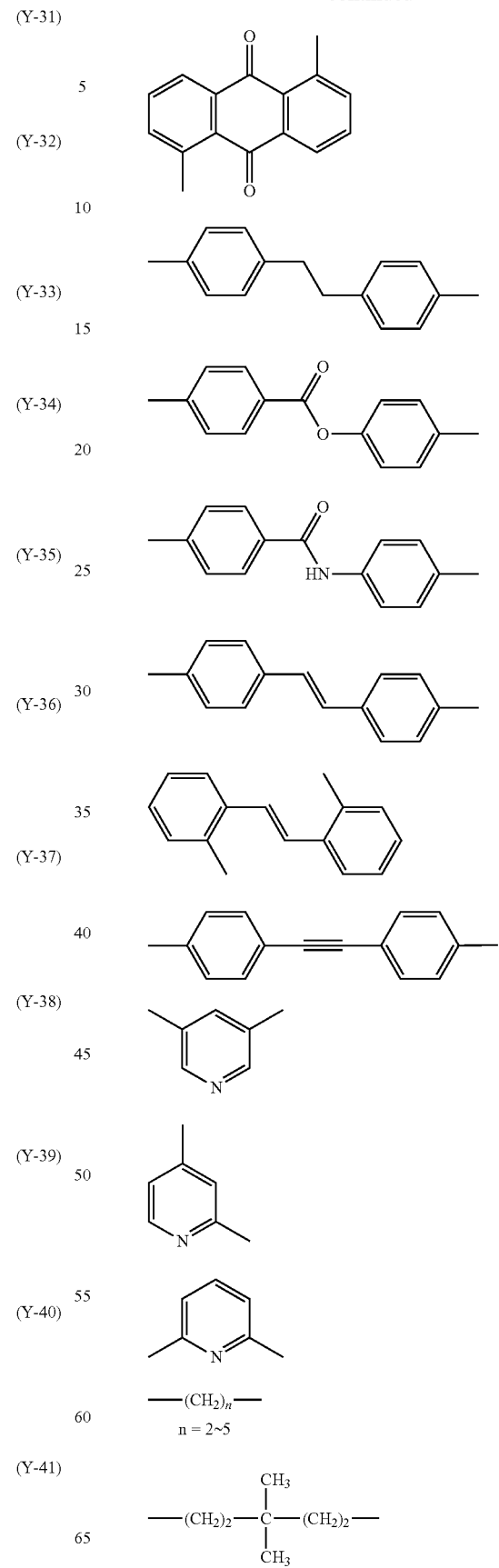

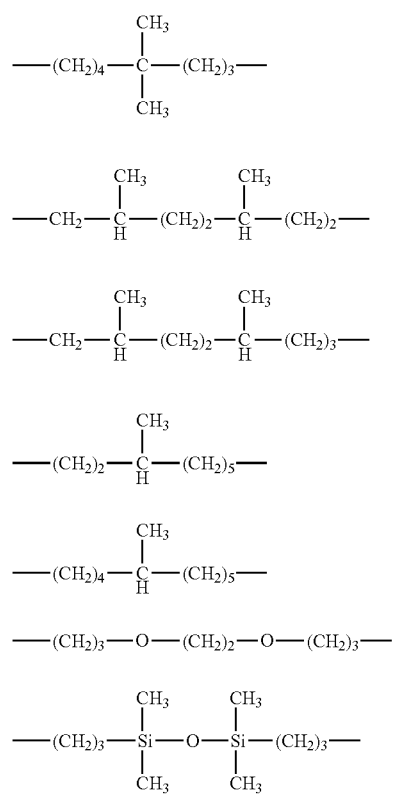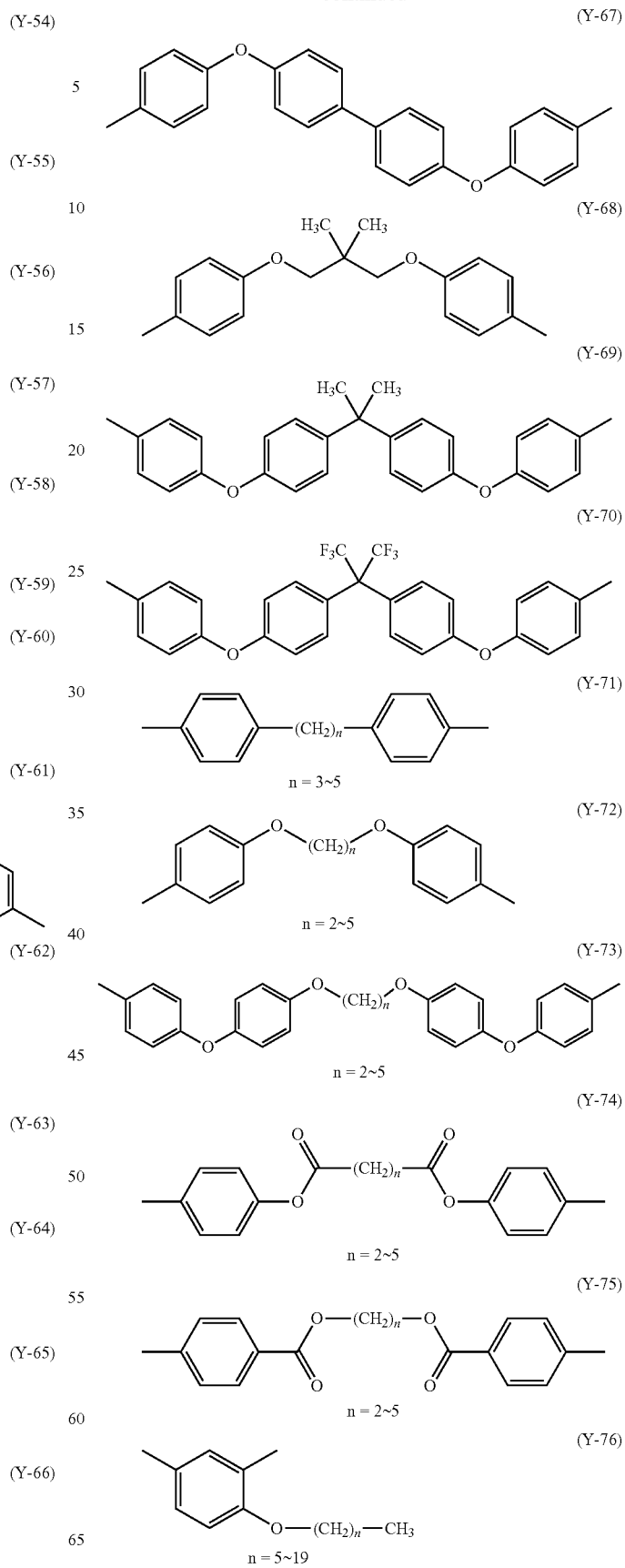

(Y-77)
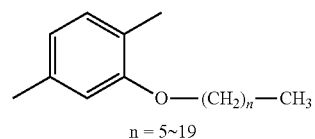
n = 5~19
(Y-78)
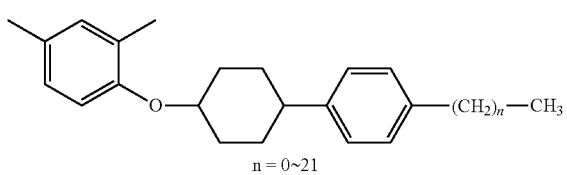
n = 0~21
(Y-79)
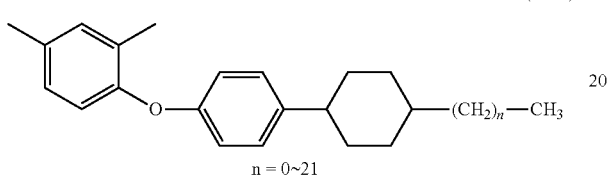
n = 0~21
(Y-80)
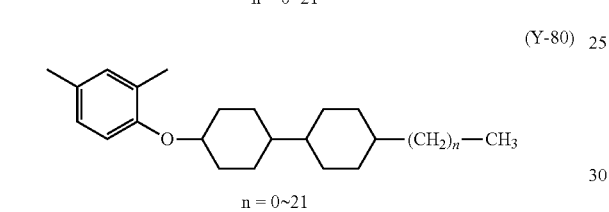
n = 0~21
(Y-81)
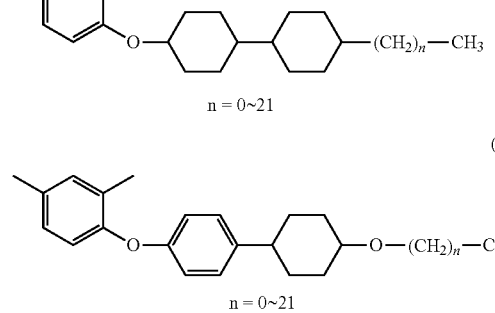
n = 0~21
(Y-82)
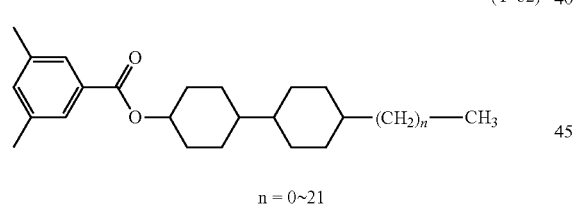
n = 0~21
(Y-83)
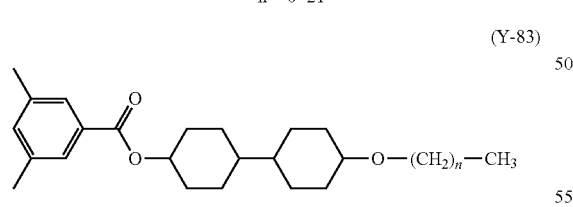
n = 0~21
(Y-84)
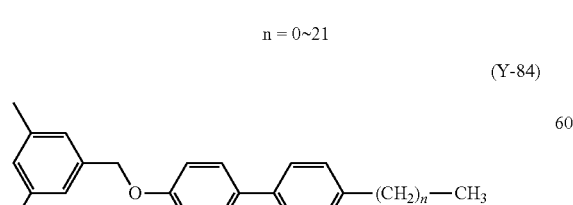
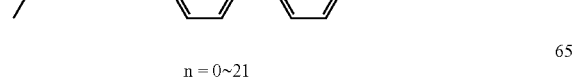
n = 0~21
(Y-85)
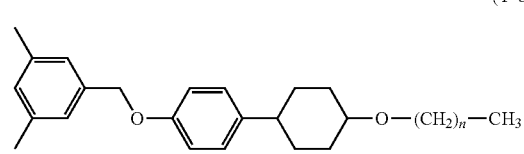
n = 0~21
(Y-86)
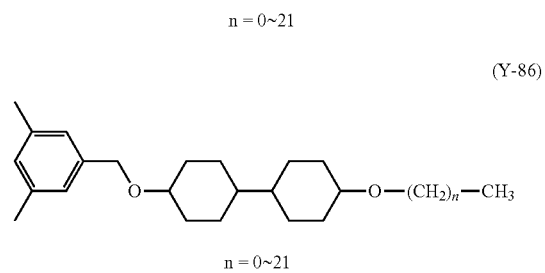
n = 0~21
(Y-87)
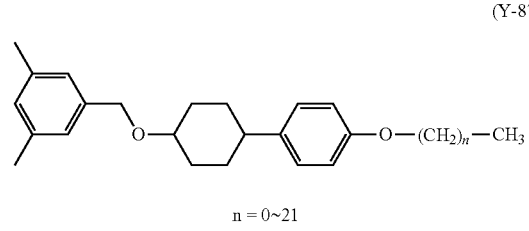
n = 0~21
(Y-88)
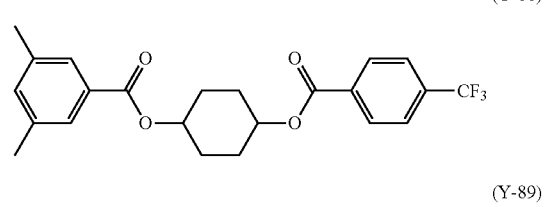
(Y-89)
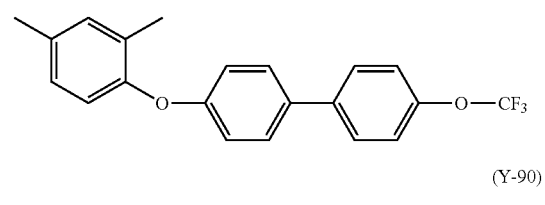
(Y-90)
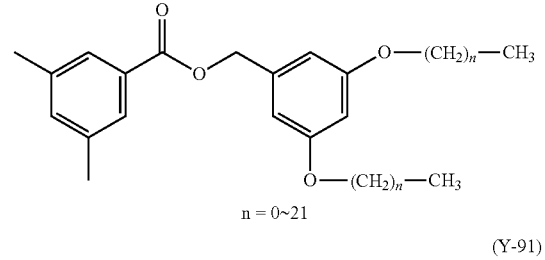
n = 0~21
(Y-91)
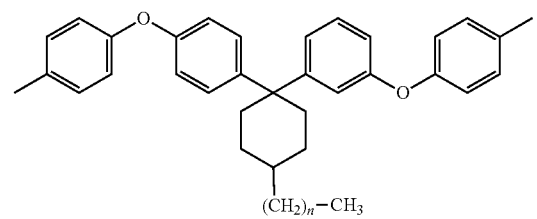
n = 0~21

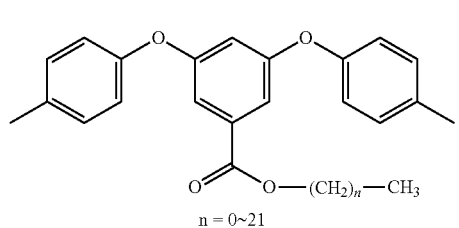
(Y-92)
n = 0~21

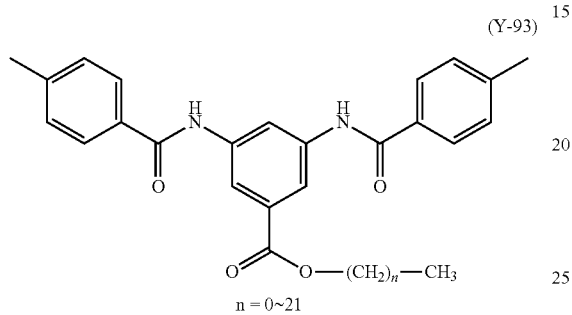
(Y-93)
n = 0~21

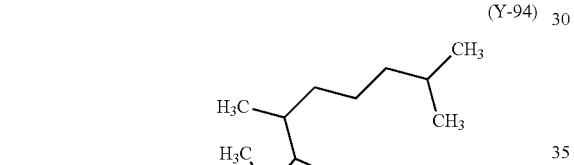
(Y-94)

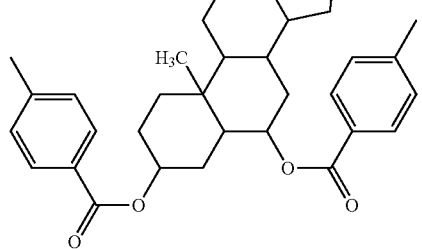
(Y-95)

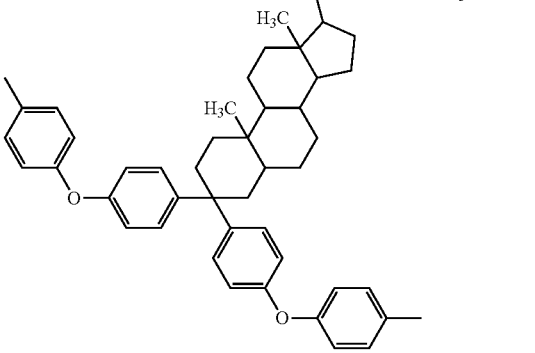
(Y-96)

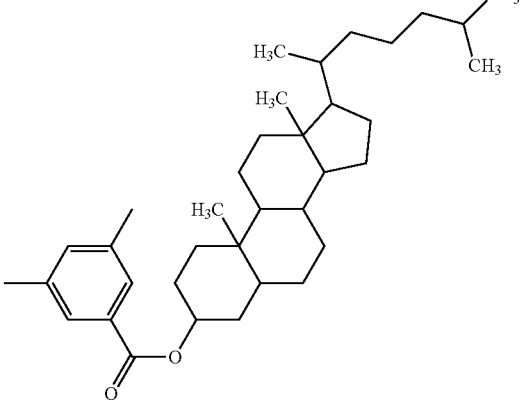
(Y-97)

As for the effect of reducing the volume resistivity of a polyimide, the basic structure of Y in formula (1) is not particularly limited. However, to impart high liquid crystal alignment properties to a liquid crystal alignment film, the structure of a portion of Y to which N—$R_2$ or N—$R_3$ is bonded is preferably an aromatic ring, and the aromatic ring is preferably a benzene ring. The structure of Y is particularly preferably a structure represented by the following formula (3).

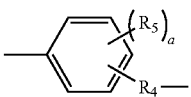
(3)

In formula (3), $R_4$ is a single bond or a $C_{1-20}$ bivalent organic group, and is preferably a single bond. $R_5$ is a structure represented by formula (2), and a is an integer of from 0 to 4.

Specific and preferred examples of Y are shown below, but the present invention is by no means limited thereto. Further, in the following structures, $R_5$ is a structure represented by formula (2), c is an integer of from 0 to 4, and each of d and e is an integer of from 0 to 2.

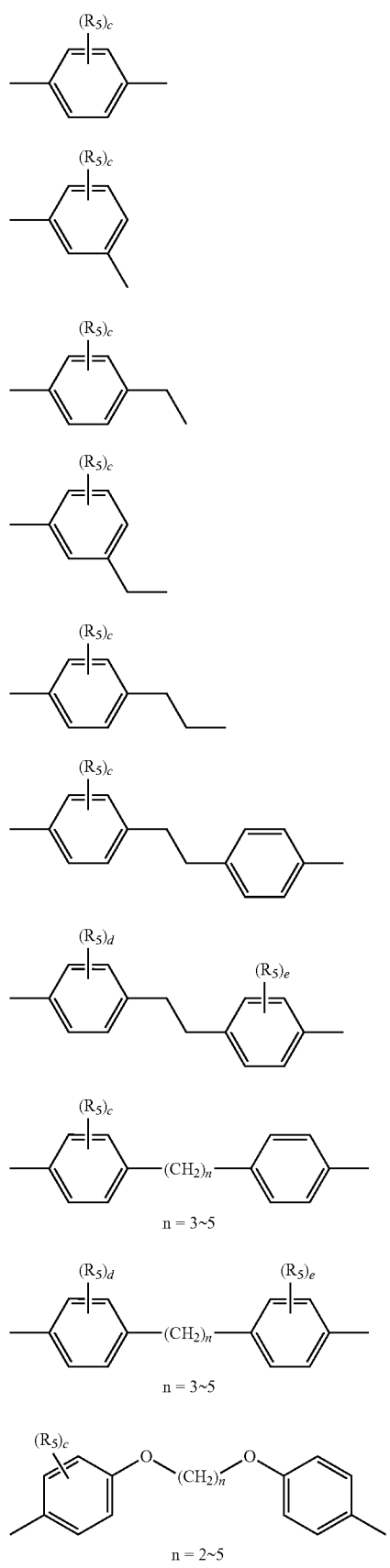
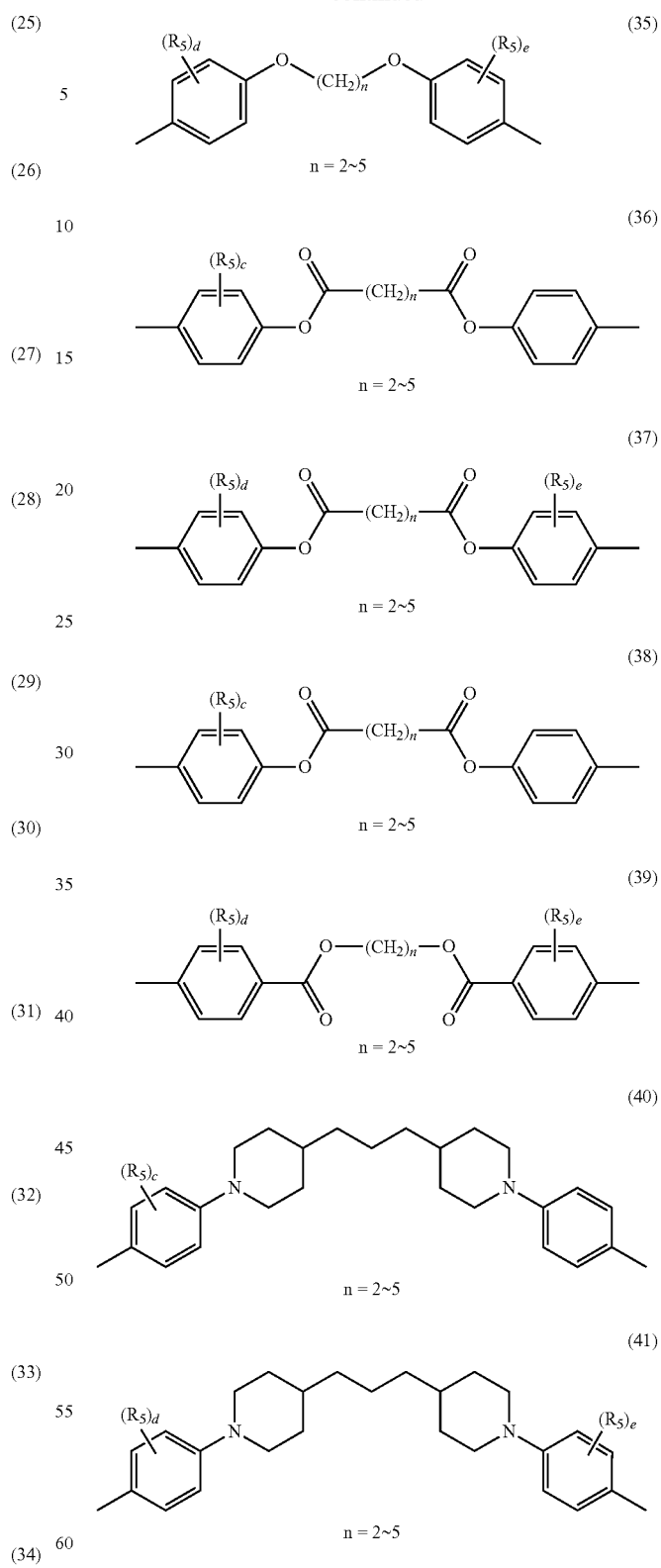
The polyimide precursor of the present invention can be obtained by reacting any one of tetracarboxylic acid derivatives represented by the following formulae (42) to (44) and a diamine compound represented by formula (45).

(42)

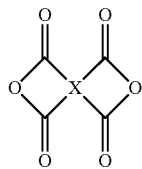

(43)

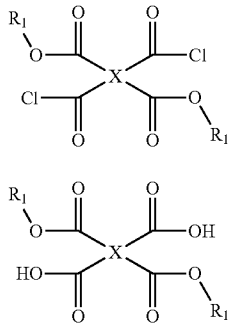

(44)

(45)

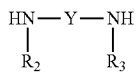

(Wherein R₁ to R₃, X and Y are the same as in formula (1).)

For example, to obtain a structure unit in which X of formula (1) has a group represented by formula (2), a tetracarboxylic acid derivative in which X in any one of the above formulae (42) to (44) has a structure having a group represented by formula (2) may be used.

Further, to obtain a structure unit in which Y of formula (1) has a group represented by formula (2), a diamine compound in which Y in the above (45) has a structure of having a group represented by formula (2) may be used.

Likewise, to obtain a structure unit in which $R_2$, $R_3$ or each of them in formula (1) is a group represented by formula (2), a diamine compound in which $R_2$, $R_3$ or each of them in the above (45) is a group represented by formula (2) may be used.

Each of X and $R_1$ in tetracarboxylic acid derivatives represented by formulae (42) to (44), and each of Y and $R_2$ to $R_3$ in a diamine compound represented by formula (45) may have the same structures as their corresponding ones in the structure of formula (1) to be obtained. Accordingly, their specific and preferred examples may be the same structures as ones exemplified in the description of formula (1).

[Preparation of Polyimide Precursor 1 (Preparation of Polyamic Acid)]

The polyamic acid can be prepared by reacting a tetracarboxylic acid dianhydride and a diamine compound.

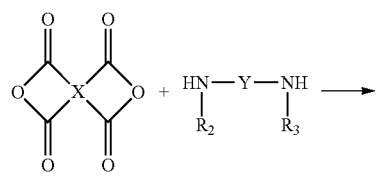

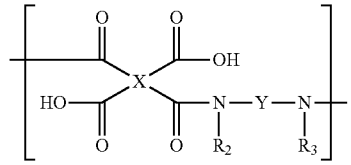

Specifically, it is prepared by reacting a tetracarboxylic acid dianhydride and a diamine in the presence of an organic solvent at from −20 to 150° C., preferably from 0 to 50° C., for from 30 minutes to 24 hours, preferably from 1 to 12 hours.

The solvent to be used for the above reaction is preferably N,N-dimethylformamide, N-methyl-2-pyrrolidone or γ-butyrolactone from the solubility of the monomer and polymer, and such solvents may be used alone or in combination of two or more of them. The concentration during the preparation is preferably from 1 to 30 mass %, more preferably from 5 to 20 mass %, from the viewpoint that precipitation of the polymer is unlikely to occur and a high molecular weight polymer is easily obtainable.

The polyamic acid thus obtained may be poured into a poor solvent while stirring the reaction solution thoroughly, whereby the polymer may be precipitated and collected. Further, such precipitation may be carried out several times, followed by washing with the poor solvent and drying at room temperature or under heating, thereby to obtain a purified powder of the polyamic acid. The poor solvent is not particularly limited, and it may, for example, be water, methanol, ethanol, hexane, butylcellosolve, acetone or toluene.

[Preparation of Polyimide Precursor 2 (Preparation of Polyamic Acid Ester)]

The polyamic acid ester can be prepared by the following methods (A) to (C).

(A) A Case of Preparing a Polyamic Acid Ester from a Polyamic Acid

The polyamic acid ester can be prepared by esterification of a polyamic acid obtained from a tetracarboxylic acid dianhydride and a diamine.

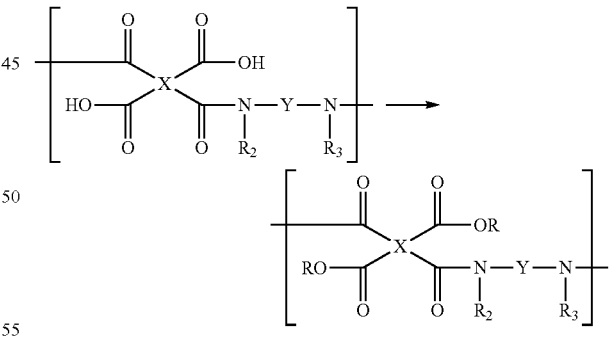

Specifically, it can be prepared by reacting the polyamic acid and an esterification agent in the presence of an organic solvent at from −20 to 150° C., preferably at from 0 to 50° C., for from 30 minutes to 24 hours, preferably from 1 to 4 hours.

The esterification agent is preferably one which can be removed easily by purification, and may, for example, be N,N-dimethylformamide dimethylacetal, N,N-dimethylformamide diethylacetal, N,N-dimethylformamide dipropylacetal, N,N-dimethylformamide dineopentylbutylacetal, N,N-dimethylformamide di-t-butylacetal, 1-methyl-3-p-tolyltriazene, 1-ethyl-3-p-tolyltriazene or 1-propyl-3-p- tolyltriazene. The amount of the esterification agent to be added is preferably from 2 to 6 mol equivalent to 1 mol of the polyamic acid repeating unit.

The solvent to be used for the above reaction is preferably N,N-dimethylformamide, N-methyl-2-pyrrolidone or γ-butyrolactone from the solubility of the polymer, and such solvents may be used alone or in combination of two or more of them. The concentration during the preparation is preferably from 1 to 30 mass %, more preferably from 5 to 20 mass %, from the viewpoint that precipitation of the polymer is unlikely to occur and a high molecular weight polymer is easily obtainable.

(B) A Case of Preparing a Polyamic Acid Ester from a Tetracarboxylic Acid Diester Dichloride and a Diamine The polyamic acid ester can be prepared from a tetracarboxylic acid diester dichloride and a diamine.

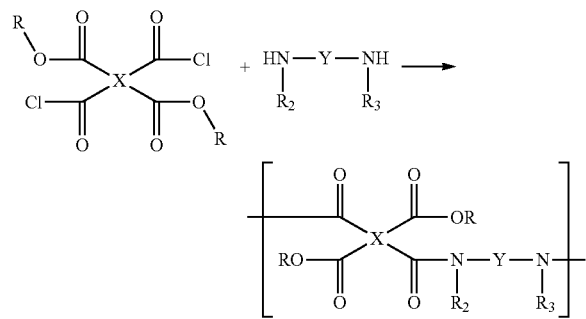

Specifically, it can be prepared by reacting the tetracarboxylic acid diester dichloride and the diamine in the presence of a base and an organic solvent at from to 150° C., preferably from 0 to 50° C., for from 30 minutes to 24 hours, preferably from 1 to 4 hours.

As the base, pyridine, triethylamine, 4-dimethylaminopyridine or the like may be used, and pyridine is preferred since the reaction proceeds mildly. The amount of the base to be added is preferably from 2 to 4 times by mole to the tetracarboxylic acid diester dichloride from the viewpoint of its removability and the obtainability of a high molecular weight polymer.

The solvent to be used for the above reaction is preferably N-methyl-2-pyrrolidone or γ-butyrolactone from the solubility of the monomer and polymer, and such solvents may be used alone or in combination of two or more of them. The concentration during the preparation is preferably from 1 to 30 mass %, more preferably from 5 to 20 mass %, from the viewpoint that precipitation of the polymer is unlikely to occur and a high molecular weight polymer is easily obtainable. Further, in order to prevent hydrolysis of the tetracarboxylic acid diester dichloride, the solvent to be used for the preparation of a polyamic acid ester is preferably dehydrated as much as possible, and it is preferred to carry out the reaction in a nitrogen atmosphere to prevent inclusion of the external air.

(C) A Case of Preparing a Polyamic Acid from a Tetracarboxylic Acid Diester and a Diamine The polyamic acid ester can be prepared via condensation of a tetracarboxylic acid diester and a diamine by a condensing agent.

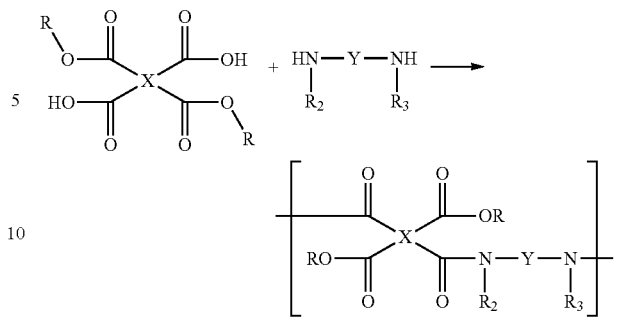

Specifically, it can be prepared by reacting the tetracarboxylic acid diester and the diamine in the presence of a condensing agent, a base and an organic solvent at from 0 to 150° C., preferably at from 0 to 100° C., for from 30 minutes to 24 hours, preferably for from 3 to 15 hours.

As the condensing agent, triphenyl phosphite, dicyclohexylcarbodiimide, 1-ethyl-3-(3-dimethylaminopropyl)carbodiimide hydrochloride, N,N'-carbonyldiimidazole, dimethoxy-1,3,5-triazinylmethylmorpholinium, O-(benzotriazol-1-yl)-N,N,N',N'-tetramethyluronium tetrafluoroborate, O-(benzotriazol-1-yl)-N,N,N',N'-tetramethyluronium hexafluorophosphate or (2,3-dihydro-2-thioxo-3-benzoxazolyl)diphenylphosphonate may, for example, be used. The amount of the condensing agent to be added is preferably from 2 to 3 times by mole to the tetracarboxylic acid diester.

As the base, a tertiary amine such as pyridine or triethylamine may be used. The amount of the base to be added is preferably from 2 to 4 times by mole to the diamine component from the viewpoint of its removability and the obtainability of a high molecular weight polymer.

Further, the above reaction proceeds efficiently by adding a Lewis acid as an additive. The Lewis acid is preferably a lithium halide such as lithium chloride or lithium bromide. The amount of the Lewis acid to be added is preferably from 0 to 1.0 times by mole to the diamine component.

Among the above-described three polyamic acid ester preparation methods, the preparation methods of (A) and (B) are particularly preferred, since a polyamic acid ester having a high molecular weight can be obtained.

The polyamic acid ester solution thus obtained is poured into a poor solvent while being thoroughly stirred, whereby the polymer may be precipitated. Such precipitation is carried out several times, followed by washing with the poor solvent and drying at room temperature or under heating to obtain a purified powder of the polyamic acid ester. The poor solvent is not particularly limited, and it may, for example, be water, methanol, ethanol, hexane, butylcellosolve, acetone or toluene.

[Molecular Weight]

The molecular weight of the polyimide precursor is influential over the viscosity of a varnish or the physical strength of a polyimide film. Its weight average molecular weight is preferably at most 500,000 from the viewpoint of the application efficiency of the varnish and the uniformity of the coating film, and is preferably at least 2,000 from the viewpoint of obtaining a polyimide film having a sufficient strength. The weight average molecular weight is more preferably from 5,000 to 300,000, further preferably from 10,000 to 100,000. The molecular weight of the polyimide precursor can be controlled by adjusting the ratio of the diamine component and the tetracarboxylic acid derivative to be used for the above-described polymerization reaction. The ratio of "the diamine component:the tetracarboxylic acid derivative" may, for example, be from 1:0.7 to 1:1.2 by molar ratio. As the molar ratio becomes closer to 1:1, the molecular weight of the obtainable polymer becomes large.

[Preparation of Polyimide]

The polyimide of the present invention can be prepared by imidation of the above-described polyimide precursor. The simple method for preparing a polyimide from a polyimide precursor is a chemical imidation method wherein a catalyst is added to the above-described polyamic acid solution obtained by reaction of the diamine component and the tetracarboxylic acid dianhydride, and is preferred since imidation reaction proceeds at a relatively low temperature, whereby decrease in the molecular weight of a polymer during imidation is unlikely to occur.

Such a chemical imidation can be carried out by stirring a polymer to be imidated in an organic solvent in the presence of a base catalyst and an acid anhydride. As the organic solvent, the above-described solvent to be used for the polymerization reaction may be used. The base catalyst may, for example, be pyridine, triethylamine, trimethylamine, tributylamine or trioctylamine. Among them, pyridine is preferred since it has an appropriate basicity to proceed the reaction. Further, the acid anhydride may, for example, be acetic anhydride, trimellitic acid anhydride or pyromellitic acid anhydride. Among them, acetic anhydride is preferred since purification after completion of the reaction becomes easier.

The temperature for the imidation reaction is from −20 to 200° C., preferably from 0 to 180° C., and the reaction time is from 1 to 100 hours. The amount of the basic catalyst is from 0.5 to 30 times by mole, preferably from 2 to 20 times by mole, to the amount of the amic acid group. The amount of the acid anhydride is from 1 to 5 times by mole, preferably from 3 to 30 times by mole to the amount of the amic acid group. The imidation ratio of the obtainable polymer can be controlled by adjusting the amount of the catalyst, the temperature and the reaction time. Since the catalyst etc. added are remained in the solution after imidation reaction, it is preferred that the obtained imidation polymer is recovered by the after-mentioned means, followed by redissolution in an organic solvent, to prepare the liquid crystal aligning agent of the present invention.

The polyimide solution thus obtained is poured into a poor solvent while being thoroughly stirred, whereby the polymer may be precipitated. Such precipitation is carried out several times, followed by washing with the poor solvent and drying at room temperature or under heating to obtain a purified powder of the polyimide. The poor solvent is not particularly limited, and it may, for example, be methanol, acetone, hexane, butylcellosolve, heptane, methyl ethyl ketone, methylisobutyl ketone, ethanol, toluene or benzene.

[Liquid Crystal Aligning Agent]

The liquid crystal aligning agent of the present invention is a coating liquid containing at least either one of thus obtained polyimide precursor or polyimide, and is used for forming a liquid crystal alignment film.

The liquid crystal aligning agent of the present invention may contain two or more types of the polyimide precursor or two or more types of the polyimide, or each of the polyimide precursor and the polyimide. Further, it may contain a polymer component other than the polyimide precursor of the present invention or the polyimide of the present invention.

The most simple configuration example of the liquid crystal aligning agent of the present invention may be a composition containing a polymer component selected from the above-described polyimide precursor and polyimide, and an organic solvent dissolving it. Such a composition may be the reaction solution itself at the time when the polyimide precursor or the polyimide is prepared, or one in which the reaction solution is diluted by the after-mentioned solvent. Further, in a case where the polyimide precursor or the polyimide is recovered as a powder, it may be a polymer solution prepared by dissolving the powder in an organic solvent.

The concentration (content) of the polyimide precursor and/or the polyimide in an organic solvent is preferably from 10 to 30 mass %, particularly preferably from 10 to 15 mass %. Further, they may be heated at the time of dissolving them. The heating temperature is preferably from 20 to 150° C., particularly preferably from 20 to 80° C.

The organic solvent to be used for dissolving the polyimide precursor or the polyimide is not particularly limited so long as it can dissolve the polymer component uniformly. Its specific examples may, for example, be N,N-dimethylformamide, N,N-diethylformamide, N,N-dimethylacetamide, N-methyl-2-pyrrolidone, N-ethyl-2-pyrrolidone, N-methylcaprolactam, 2-pyrrolidone, N-vinyl-2-pyrrolidone, dimethylsulfoxide, dimethylsulfone, γ-butyrolactone, 1,3-dimethylimidazolidinone, 3-methoxy-N,N-dimethylpropanamide. They may be used alone, or two or more of them may be used as mixed. Further, even a solvent which is not capable of dissolving the polymer component alone may be used within a range where the polymer will not be precipitated.

The solvent component of the liquid crystal aligning agent of the present invention may contain a solvent to improve the uniformity of a coating film at the time of applying the liquid crystal aligning agent on a substrate, in addition to the organic solvent to be used for dissolving the polymer component. As such a component, a solvent having a surface tension lower than the above-described organic solvent is usually used. As its specific examples, ethylcellosolve, butylcellosolve, ethyl carbitol, butyl carbitol, ethyl carbitol acetate, ethylene glycol, 1-methoxy-2-propanol, 1-ethoxy-2-propanol, 1-butoxy-2-propanol, 1-phenoxy-2-propanol, propylene glycol monoacetate, propylene glycol diacetate, propylene glycol-1-monomethyl ether-2-acetate, propylene glycol-1-monoethyl ether-2-acetate, dipropylene glycol, 2-(2-ethoxypropoxy) propanol, lactic acid methyl ester, lactic acid ethyl ester, lactic acid n-propyl ester, lactic acid n-butyl ester and lactic acid isoamyl ester may, for example, be mentioned. Two or more of such solvents may be used in combination.

The concentration of the polymer in the liquid crystal aligning agent of the present invention may suitably be changed depending upon the thickness set for the liquid crystal alignment film to be formed, but it is preferably at least 1 mass % from the viewpoint of forming a uniform coating film free from defects, and preferably at most 10 mass % from the viewpoint of the storage stability of the solution.

Additionally, the liquid crystal aligning agent of the present invention may contain various additives such as a silane coupling agent and a crosslinking agent.

Such a silane coupling agent is added to improve the adhesion of the substrate to be applied with the liquid crystal aligning agent, to the liquid crystal alignment film formed thereon. Now, specific examples of the silane coupling agent will be mentioned, but it should be understood that the silane coupling agent which can be used for the liquid crystal aligning agent of the present invention is by no means limited thereto.

An amine type silane coupling agent such as 3-aminopropyltriethoxysilane, 3-(2-aminoethyl)aminopropyltrimethoxysilane, 3-(2-aminoethyl)aminopropylmethyldimethoxysilane, 3-aminopropyltrimethoxysilane, 3-phenylaminopropyltrimethoxysilane, 3-triethoxysilyl-N-(1,3-dimethyl-butylidene)propylamine or 3-aminopropyldiethoxymethylsilane; a vinyl type silane coupling agent such as vinyltrimethoxysilane, vinyltriethoxysilane, vinyltris(2-methoxyethoxy)silane, vinylmethyldimethoxysilane, vinyltriacetoxysilane, vinyltriisopropoxysilane, allyltrimethoxysilane or p-styryltrimethoxysilane; an epoxy type silane coupling agent such as 3-glycidoxypropyltrimethoxysilane, 3-glycidoxypropyltriethoxysilane, 3-glycidoxypropylmethyldiethoxysilane, 3-glycidoxypropylmethyldimethoxysilane or 2-(3,4-epoxycyclohexyl)ethyltrimethoxysilane; a methacryl type silane coupling agent such as 3-methacryloxypropylmethyldimethoxysilane, 3-methacryloxypropyltrimethoxysilane, 3-methacryloxypropylmethyldiethoxysilane or 3-methacryloxypropyltriethoxysilane; an acryl type silane coupling agent such as 3-acryloxypropyltrimethoxysilane; a ureido type silane coupling agent such as 3-ureido propyltriethoxysilane; a sulfide type silane coupling agent such as bis(3-(triethoxysilyl)propyl)disulfide or bis(3-(triethoxysilyl)propyl)tetrasulfide; a mercapto type silane coupling agent such as 3-mercaptopropylmethyldimethoxysilane, 3-mercaptopropyltrimethoxysilane or 3-octanoylthio-1-propyltriethoxysilane; an isocyanate type silane coupling agent such as 3-isocyanate propyltriethoxysilane or 3-isocyanate propyltrimethoxysilane; an aldehyde type silane coupling agent such as triethoxysilyl butylaldehyde; a carbamate type silane coupling agent such as triethoxysilyl methylcarbamate or (3-triethoxysilylpropyl)-t-butylcarbamate.

The amount of the silane coupling agent to be added is preferably from 0.01 to 5.0 mass %, more preferably from 0.1 to 1.0 mass %, to the amount of a polymer component, from the viewpoint of preventing an adverse effect to the liquid crystal alignment properties caused by the unreacted one while achieving the adhesion improvement effect. Addition of the silane coupling agent may be preferably carried out before introducing the above-described solvent to improve the uniformity of a coating film, to prevent precipitation of the polymer.

[Liquid Crystal Alignment Film]

The liquid crystal alignment film of the present invention is a coating film obtained by applying the liquid crystal aligning agent obtained as described above on a substrate, followed by drying and baking, and as the case requires, the surface of the coating film is subjected to a rubbing or photo-alignment treatment.

The substrate to be applied with the liquid crystal aligning agent of the present invention is not particularly limited so long as it has a high transparency, and may, for example, be a glass substrate, a silicon nitride substrate, or a plastic substrate such as an acryl substrate or a polycarbonate substrate, and is preferably a substrate on which ITO electrodes etc. are formed for liquid crystal driving, in view of the simplicity of the process. For a reflective type liquid crystal display element, an opaque substrate such as a silicon wafer may be used as the substrate when it is used for only one side, and a light reflecting material such as aluminum may be used for its electrodes. The method for application of the liquid crystal aligning agent may, for example, be a spin coating method, a printing method or an ink jetting method. In the drying and baking steps after applying the liquid crystal aligning agent, optional temperatures and times may be selected for use. Usually, in order to sufficiently remove the contained organic solvent, the drying is carried out at from 50 to 120° C. for from 1 to 10 minutes, followed by baking at from 150 to 300° C. for from 5 to 120 minutes. The thickness of the coating film after baking is not particularly limited, and is from 5 to 300 nm, preferably from 10 to 200 nm, since the reliability of the liquid crystal display element is likely to be low if it is too thin.

The rubbing treatment can be carried out by using a conventional rubbing apparatus. For the material of a rubbing cloth for the treatment, cotton, nylon and rayon may, for example, be mentioned. The condition for the rubbing treatment is usually such a condition that the rotational speed is from 300 to 2,000 rpm, the advancing speed is from 5 to 100 mm/s and the pushing amount is from 0.1 to 1.0 mm. After that, residues caused by the rubbing treatment are removed by ultrasonic washing with pure water or an alcohol.

As a specific example of the photo-alignment treatment method, a method wherein a radiation polarized in a constant direction is applied on the above-described coating film surface may be mentioned, and as the case requires, heat treatment at from 150 to 250° C. is further carried out, to impart the liquid crystal alignment function. As the radiation, ultraviolet rays having a wavelength of from 100 nm to 800 nm and visible light may be employed. Among them, ultraviolet rays having a wavelength of from 100 nm to 400 nm are preferred, and ones having a wavelength of from 200 nm to 400 nm are particularly preferred. Further, in order to improve the liquid crystal alignment properties, the radiation may be applied while heating the coating film substrate at from 50 to 250° C. The amount of the radiation to be applied is preferably within a range of from 1 to 10,000 $mJ/cm^2$, particularly preferably within a range of from 100 to 5,000 $mJ/cm^2$.

[Liquid Crystal Display Element]

The liquid crystal display element of the present invention is a liquid crystal display element obtained by preparing a substrate equipped with a liquid crystal alignment film from the liquid crystal aligning agent of the present invention by the above-described method, and then forming a liquid crystal cell by a known method.

The production process of the liquid crystal cell is not particularly limited, and as one example, a method wherein a pair of substrates on which a liquid crystal alignment film is formed are installed to sandwich a spacer of preferably from 1 to 30 μm, more preferably from 2 to 10 μm, with the liquid crystal alignment film side located inside, followed by fixing their periphery by a sealing agent, and liquid crystal is injected and sealed, may be mentioned. The method for sealing liquid crystal is not particularly limited, and may, for example, be a vacuum method wherein liquid crystal is introduced after the inside of the prepared liquid crystal cell is depressurized or a dropping method wherein sealing is carried out after dropping of liquid crystal.

[Measurement of Volume Resistivity]

The measurement method of the volume resistivity the liquid crystal alignment film of the present invention is not particularly limited, and the following method may be mentioned as one example.

The above-described liquid crystal aligning agent is applied on a glass substrate provided with ITO transparent electrodes by a spin coat method. In the drying and baking steps after the application, optional temperatures and times may be selected, and it is preferred to carry out drying at from 50 to 120° C. for from 1 to 10 minutes, followed by baking at from 150 to 300° C. for from 5 to 120 minutes, like in a general alignment film forming process. The thickness of the coating film after baking is not particularly limited, and is preferably from 50 to 2,000 nm, more preferably from 100 to 1,000 nm, from the viewpoint of pinholes generation caused by fine particles, easiness in preparation and reflection of the actual physical properties of the liquid crystal alignment film. After that, electrodes are formed on the surface of the coating film. The electrodes are preferably aluminum electrodes which can be prepared simply by vapor deposition without damaging the coating film. The electrode area is preferably from 0.001 $cm^2$ to 0.05 $cm^2$ from the viewpoint that pinholes in the coating film are unlikely to be contained and application of large voltage is not required at the time of measurement. To the prepared element, a constant voltage is applied, whereby the volume resistivity can be calculated from the current value. The application voltage is preferably from 1 to 20 V from the viewpoint of easiness in measurement of the current value and unlikeliness of short circuiting.

[Evaluation of Image Sticking Properties]

The evaluation method of the image sticking properties of the liquid crystal display element of the present invention is not particularly limited, and a dielectric absorption method wherein a residual voltage after application of DC voltage to a liquid crystal cell is measured may be mentioned as one example.

The above-described liquid crystal aligning agent is applied on a glass substrate provided with ITO transparent electrodes by a spin coating method. In the drying and baking steps after application, optional temperatures and times may be selected, and it is preferred to carry out drying at from 50 to 120° C. for from 1 to 10 minutes, followed by baking at from 150 to 300° C. for from 5 to 120 minutes, like in a general alignment film forming process. The thickness of the coating film after baking is not particularly limited, and is from 5 to 300 nm, preferably from 10 to 200 nm, like in a general alignment film forming process. The surface of the coating film was subjected to an alignment treatment by rubbing to obtain a substrate provided with a liquid crystal alignment film. Two such substrates each provided with a liquid crystal alignment film were prepared, and on the liquid crystal alignment film surface of one of the substrates, a spacer of from 4 to 6 μm was scattered. Then, a sealing agent is printed thereon, another substrate was overlaid so that the liquid crystal alignment films face to each other and the rubbing directions become orthogonal to each other, and then the sealing agent was cured to prepare a vacant cell. To this vacant cell, liquid crystal is injected by a vacuum-injection method, and the injection inlet is sealed to obtain a twist nematic liquid crystal cell.

To the twist nematic liquid crystal cell, DC voltage of 10 V was applied for 30 minutes at an optional temperature, and after a 1 second short-circuit, the time dependent change of an electrical potential generated in the liquid crystal cell is measured.

[Specific Diamine]

In the preparation of the polyimide precursor of the present invention, from the viewpoint of the simplicity at the time of preparing a monomer to be used as a starting material of the polyimide precursor and handling efficiency of the monomer, it is preferred to use a diamine compound having a group wherein Y in the above formula (45) is a group represented by formula (2), or a diamine compound in which a group represented by formula (2) is bonded to $R_2$, $R_3$ or each of them in the above formula (45). Among such diamine compounds, a diamine compound represented by the following formula (4) or formula (5) is preferred, since e.g. the liquid crystal alignment film obtained therefrom has high liquid crystal alignment properties, and a liquid crystal display element having strong mechanical properties, a low volume resistivity and an excellent residual DC property can be obtained therefrom.

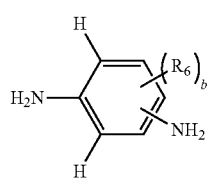

(4)

(Wherein $R_6$ is a structure represented by the above formula (2). b is 1 or 2.)

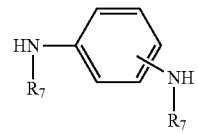

(5)

(Wherein $R_7$ is a structure represented by the above formula (2).)

Each of the diamine compounds of the following formulae (A) to (D) is a particularly preferred compound among diamine compounds represented by the above formula (4) or formula (5), since it can be prepared relatively easily.

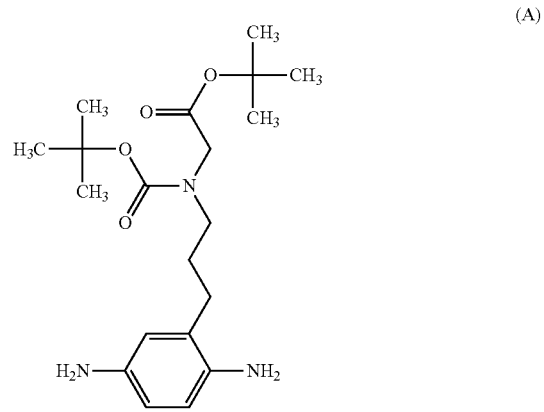 [SMILES: CC(C)(C)OC(=O)CN(CCCc1cc(N)ccc1N)C(=O)OC(C)(C)C]

(A)

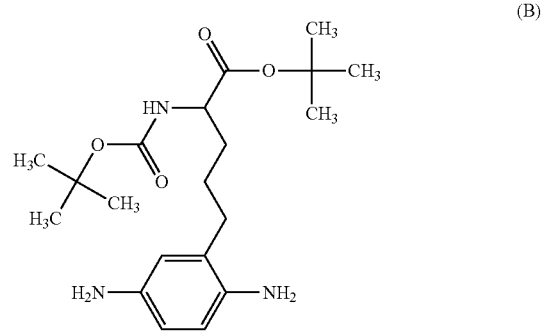 [SMILES: CC(C)(C)OC(=O)NC(CCCc1cc(N)ccc1N)C(=O)OC(C)(C)C]

(B)

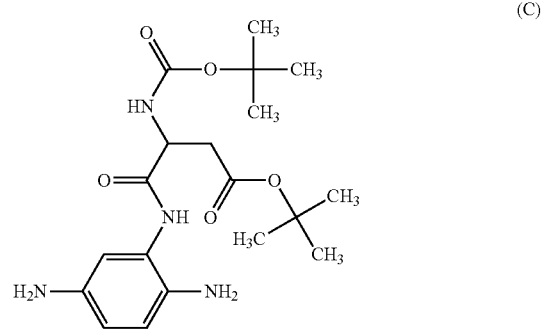

(C)

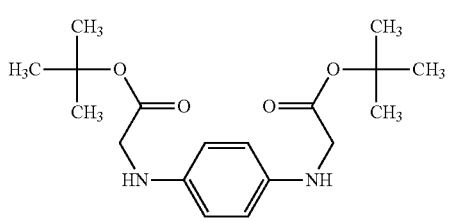

(D)

[Specific Diamine]

Each of the diamine compounds of the above formulae (A) to (D) can be prepared as follows.

Specific Diamine Compound (A)

The diamine compound of formula (A) can be prepared via, e.g. the following 4-steps pathway by using propargylamine of the following formula (A1), t-butyl bromoacetate of formula (A2), di-t-butyl bicarbonate of formula (A3) and 2-iodo-4-nitroaniline of formula (A4) as the main starting materials.

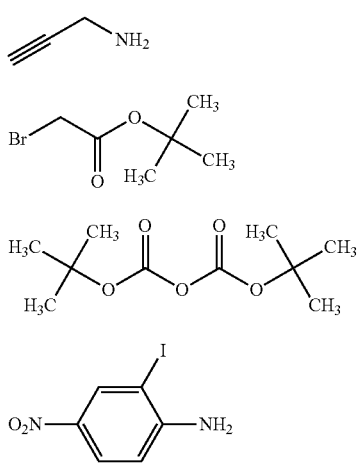

(A1)

(A2)

(A3)

(A4)

Step 1: Preparation of Compound (A5)

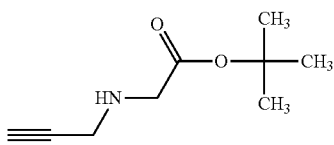

(A5)

Propargylamine of formula (A1) is dissolved in an organic solvent, and then a base is added. Here, the organic solvent to be used is preferably a polar solvent commonly used for a nucleophilic substitution reaction, and as specific examples, N,N-dimethylformamide, dimethylsulfoxide, acetone, tetrahydrofuran, methanol and ethanol may, for example, be mentioned, but it is not limited thereto. Further, as the base, potassium hydroxide, sodium hydroxide, potassium carbonate, sodium carbonate, sodium hydrogencarbonate, sodium hydride, triethylamine, diisopropylethylamine, pyridine and 4-(N,N-dimethylamino)pyridine may, for example, be mentioned, but it is not limited thereto. Then, the solution is adjusted to a temperature of from −40 to 70° C., preferably from −20 to 20° C., and then while stirring the reaction solution, t-butylbromoacetate of formula (A2) is added in an amount of from 0.1 to 1.0 time by mole, preferably from 0.5 to 0.8 time by mole to increase yield, to the amount of propargylamine. At the time of the addition, it is preferably diluted with the same solvent as that of the reaction solution, and then dropwise added. Then, the reaction solution stirred for from 1 to 48 hours, preferably from 2 to 24 hours, while maintaining the reaction temperature in a range of from −20 to 20° C. After completion of the reaction, the solid material in the reaction solution is filtrated, and then subjected to extraction operation with an organic solvent and water. The organic solvent to be used for the extraction operation is not particularly limited so long as it can be separated from water at a low boiling point and can dissolve an organic material easily, and may be ethyl acetate, dichloromethane, dichloroethane, diethyl ether, cyclopentyl methyl ether, t-butyl methyl ether or the like. The separated organic phase is washed with pure water or a saturated sodium chloride aqueous solution, and then dried by a drying agent. As the drying agent, sodium sulfate or magnesium sulfate is preferred. Then, the drying agent is filtrated, and the solvent of the filtrate is removed by evaporation to obtain a compound of the above formula (A5). It can be used for the next reaction without being purified, but may be purified by various methods. As the purification method, silica gel column chromatography or distillation may, for example, be mentioned.

Step 2: Preparation of Compound (A6)

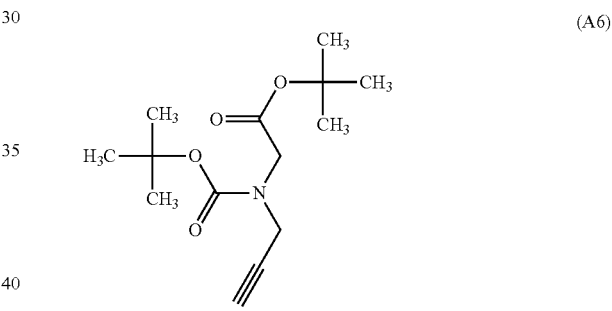

(A6)

The above compound (A5) is dissolved in an organic solvent, and di-t-butyl bicarbonate of formula (A3) is added thereto, followed by stirring at a reaction temperature of −10 to 40° C., preferably from 0 to 20° C. for from 1 to 48 hours, preferably from 2 to 24 hours. The organic solvent to be used for the reaction is not limited so long as it can dissolve compound (A5) and does not react with di-t-butyl bicarbonate, and is preferably dichloromethane or tetrahydrofuran. Further, to proceed the reaction more efficiently, an organic base such as triethylamine or pyridine may be added. The amount of the addition is preferably from 1 to 2 times by mole to the amount of compound (A5). After completion of the reaction, extraction operation is carried out by using an organic solvent, pure water or a saturated sodium chloride aqueous solution, and then a drying agent is added to the obtained organic phase to dry it. The organic solvent to be used for extraction is not limited so long as it is not mixed with water, and is preferably dichloromethane. Further, water or a saturated sodium chloride aqueous solution may be added to the reaction solution to extract impurities. The drying agent is preferably sodium sulfate or magnesium sulfate. After removal of the drying agent, the solvent may be removed from the filtrate by evaporation to obtain a compound of the above formula (A6). The obtained compound may be used for the next reaction without being purified, but is preferably purified by various methods. The purification method may, for example, be silica gel column chromatography.

Step 3: Preparation of Compound (A7)

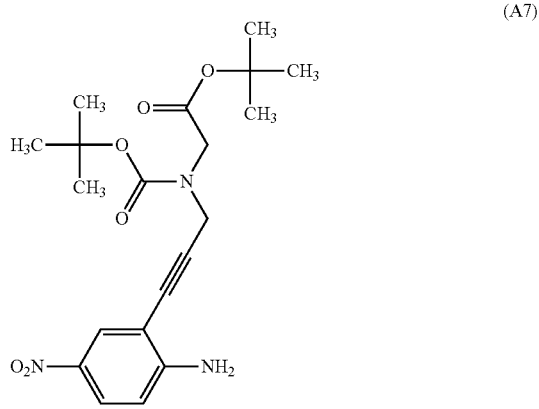

Aryl iodide of the above formula (A4), a palladium catalyst, a copper catalyst and a base are added, and dissolved to an organic solvent. The palladium catalyst is preferably bis(triphenylphosphine) palladium dichloride or tetrakis(triphenylphosphine) palladium, and its amount of addition is preferably from 0.05 to 10 mol %, more preferably from 0.1 to 5.0 mol %, to the amount of aryl iodide. The copper catalyst is preferably copper iodide, and its amount of addition is preferably from 0.05 to 10 mol %, more preferably from 0.1 to 5.0 mol %, to the amount of aryl iodide. The base is preferably triethylamine, diethylamine or diisopropylethylamine, and its amount of addition is preferably from 1 to 10 times by mole, more preferably from 5 to 8 times by mole, to the amount of aryl iodide. The organic solvent to be used for the reaction is not limited so long as it can dissolve aryl iodide and does not react with various reagents to be added thereafter, and is preferably N,N-dimethylformamide.

The reaction solution is stirred at from 0 to 40° C., preferably from 0 to 30° C. for from 5 minutes to 30 minutes, and then the above compound (A6) is added, followed by stirring for from 1 to 48 hours, preferably from 2 to 24 hours to obtain a compound of the above formula (A7). The amount of formula (A6) to be added is preferably from 1.0 to 2.0 times by mole, more preferably from 1.0 to 1.5 times by mole, to the amount of aryl iodide.

After completion of the reaction, an organic solvent and an acidic aqueous solution are introduced to the reaction solution, thereby to carry out extraction operation. The solvent to be used for the extraction is not limited so long as it can dissolve compound (A7) and is not mixed with water, and is preferably ethyl acetate, dichloromethane, chloroform or 1,2-dichloroethane. The acidic aqueous solution is preferably an aqueous solution of ammonium chloride, hydrochloric acid, acetic acid or formic acid. Since decomposition of compound occurs if its acidity is too high, an aqueous solution of ammonium chloride is more preferred. The concentration of the acidic aqueous solution is preferably from 0.5 to 2.0 mol/L, more preferably from 1.0 to 1.5 mol/L. The organic phase obtained after the extraction is washed several times with the acidic aqueous solution, and then washed with pure water or a saturated sodium chloride aqueous solution, followed by drying by a drying agent. The drying agent is preferably sodium sulfate or magnesium sulfate. The drying agent is removed by filtration, and then the solvent is removed by evaporation to obtain a crude product of compound (A7). It can be used for the next reaction without being purified, but is preferably purified by various methods. The purification method may, for example, be silica gel column chromatography, recrystallization, or washing with an organic solvent, and is preferably recrystallization from the simplicity of operation and the effectiveness of purification. The organic solvent to be used for recrystallization is not limited so long as it can recrystallize compound (A7), and a mixed solvent comprised of two or more types of organic solvents may be used for recrystallization.

Step 4: Reduction of Compound (A7)

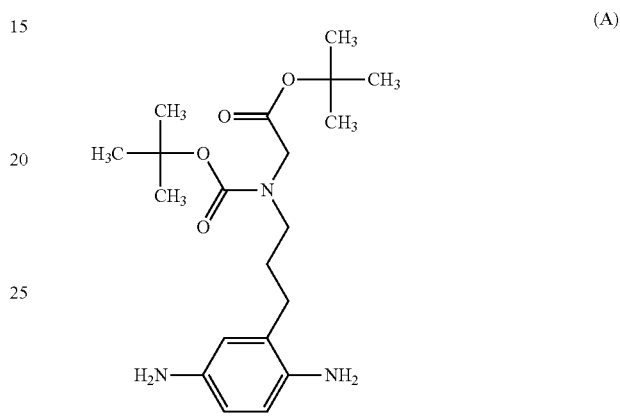

By reducing a nitro group or an ethylene group of the above compound (A7), the diamine compound of the present invention represented by the above formula (A) can be obtained. One example of the reducing method is shown below.

Compound (A7) is dissolved in an organic solvent, then the interior of the reaction vessel is substituted by nitrogen, a catalyst is added thereto, and the interior of the reaction vessel is substituted by hydrogen. Here, the organic solvent to be used is preferably methanol, ethanol, 2-propanol, tetrahydrofuran or 1,4-dioxane to let the reaction proceed more efficiently, and more preferably methanol or ethanol. The catalyst may, for example, be palladium carbon, platinum carbon or platinum oxide, but palladium carbon is more preferred due to its good reaction efficiency. The reaction solution is stirred at from 0 to 100° C., preferably from 10 to 60° C., for from 12 to 72 hours, preferably from 24 to 60 hours. After completion of the reaction, the catalyst is removed and the organic solvent is removed by evaporation, thereby to obtain a crude product of diamine (A). The obtained diamine compound is preferably purified by various methods for smooth progression of the polymerization reaction to obtain a polyimide precursor, thereby to obtain a high molecular weight polymer. The purification method may be silica gel chromatography or activated carbon treatment, and is preferably an activated carbon treatment since decomposition of the product is unlikely to occur.

Specific Diamine Compound (B)

The diamine compound of formula (B) can be prepared via the following 5-steps pathway by using N-(diphenylmethylene)glycine t-butyl ester of the following formula (B1), propargyl bromide of formula (B2), di-t-butyl bicarbonate of the above formula (A3) and 2-iodo-4-nitroaniline of formula (A4) as the main starting materials.

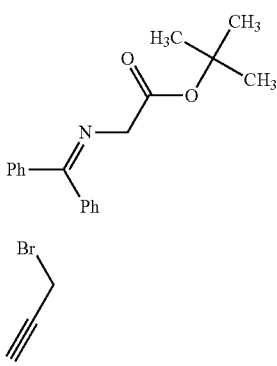

(B1)

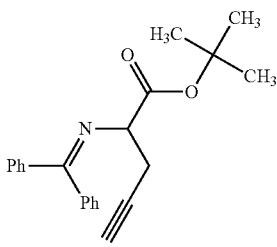

(B2)

Step 1: Preparation of Compound (B3)

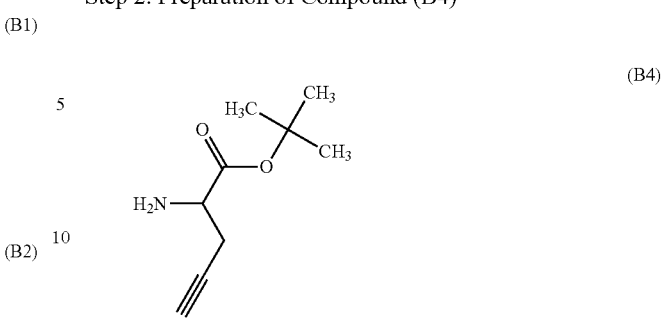

(B3)

N-(diphenylmethylene)glycine t-butyl of the above formula (B1) is dissolved in an organic solvent, and then a base is added thereto. Here, the organic solvent to be used is not limited so long as it can dissolve (B1), and is specifically dichloromethane, dichloroethane, toluene, tetrahydrofuran, N,N-dimethylformamide or the like, and two or more types of them may be mixed. Further, the base may, for example, be potassium hydroxide, sodium hydroxide, potassium carbonate, sodium carbonate, sodium hydrogencarbonate, sodium hydride, triethylamine, diisopropylethylamine, pyridine and 4-(N,N-dimethylamino)pyridine, and an aqueous solution of them may be combined with a phase-transfer catalyst. The phase-transfer catalyst may, for example, be tetrabutylammonium bromide or benzyltrimethyl ammonium chloride. Then, while stirring the solution at from 0 to 70° C., preferably from 10 to 40° C., propargyl bromide of formula (B2) is added, followed by further stirring for from 1 to 48 hours, preferably from 4 to 24 hours to obtain a compound of the above formula (B3). After completion of the reaction, a solid material in the reaction mixture is removed by filtration to carry out extraction operation with an organic solvent or water. The organic solvent to be used for the extraction is not particularly limited so long as it can be separated from water at a low boiling point and can dissolve compound (B3), and may be ethyl acetate, dichloromethane, dichloroethane, diethyl ether, cyclopentylmethyl ether, t-butyl methyl ether or the like. The separated organic phase is washed with pure water or a saturated sodium chloride aqueous solution, and then dried by a drying agent. The drying agent is preferably sodium sulfate or magnesium sulfate. Then, the drying agent is removed and the solvent is removed by evaporation, thereby to obtain a crude product of compound (B3). It may be used for the next reaction without being purified, but may be purified by various methods. The purification methods may, for example, be silica gel column chromatography.

Step 2: Preparation of Compound (B4)

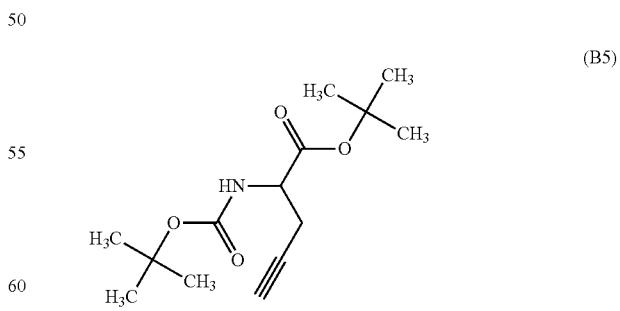

(B4)

The above compound (B3) is dissolved in an organic solvent, and then an aqueous solution of citric acid is added thereto, followed by stirring at from 0 to 100° C., preferably from 10 to 40° C., for from 1 to 12 hours, preferably from 1 to 6 hours to obtain a compound of the above formula (B4). The organic solvent to be used for the reaction is not limited so long as it can dissolve (B3), and is preferably tetrahydrofuran. After completion of the reaction, an organic solvent is added thereto, and then compound (B4) is extracted to an aqueous phase by an acidic aqueous solution, and then a base is added to the aqueous phase to make it basic, followed by extraction with an organic solvent. The organic solvent is not limited so long as it can dissolve (B4) and can be separated from water, and may be ethyl acetate, dichloromethane, dichloroethane, diethyl ether, cyclopentylmethyl ether, t-butyl methyl ether or the like. The acidic aqueous solution is not limited so long as it can dissolve compound (B4) and does not decompose (B4), and is preferably a hydrochloric acid aqueous solution. The base is not limited so long as it can separate compound (B4) from the acidic aqueous solution and does not decompose (B4), and may be sodium hydroxide, potassium hydroxide, sodium carbonate, potassium carbonate, sodium hydrogencarbonate or the like. After the extraction, the organic phase is washed with pure water or a saturated sodium chloride aqueous solution, and then a drying agent is added to the obtained organic phase to dry it. The drying agent is preferably sodium sulfate or magnesium sulfate. The drying agent is removed by filtration, and then the solvent is removed from the filtrate by evaporation, thereby to obtain compound (B4). The obtained compound can be used for the next reaction without being purified, but is preferably purified by various methods. The purification method may, for example, be silica gel column chromatography or distillation.

Step 3: Preparation of Compound (B5)

(B5)

The above compound (B4) is dissolved in an organic solvent, and di-t-butyl bicarbonate of formula (A3) is added thereto, followed by stirring at from −10 to 40° C., preferably from 0 to 30° C., for from 1 to 48 hours, preferably from 2 to 24 hours. The organic solvent to be used for the reaction is not limited so long as it can dissolve compound of formula (B4) and does not react with di-t-butyl bicarbonate, and is preferably dichloromethane or tetrahydrofuran. Further, to let the reaction proceed more efficiently, an organic base such as triethylamine or pyridine may be added thereto. The addition amount is preferably from 1 to 2 times by mole to the amount of compound (B4). After completion of the reaction, an organic solvent, pure water or a saturated sodium chloride aqueous solution is added thereto to carry out extraction operation, and then a drying agent is added to the obtained organic phase to dry it. The organic solvent to be used for the extraction is not limited so long as it can dissolve (B4) and is not mixed with water, and is preferably dichloromethane. Further, to the reaction solution, water or a saturated sodium chloride aqueous solution may be added to extract impurities. The drying agent is preferably sodium sulfate or magnesium sulfate. The drying agent is removed by filtration, and then the solvent is removed from the filtrate by evaporation, thereby to obtain a compound of the above formula (B5). The obtained compound may be used for the next reaction without being purified, but is preferably purified by various methods. The purification method may, for example, be silica gel column chromatography.

Step 4: Preparation of Compound (B6)

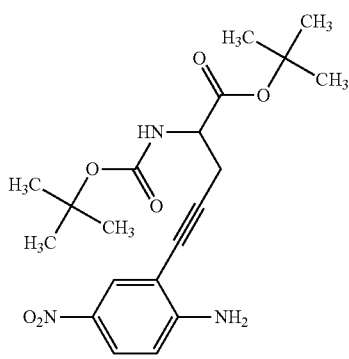

(B6)

In accordance with the above-described preparation method of compound (A7), the above compound (B5) and compound (A4) are reacted to obtain a compound of the above formula (B6).

Step 5: Reduction of Compound (B6)

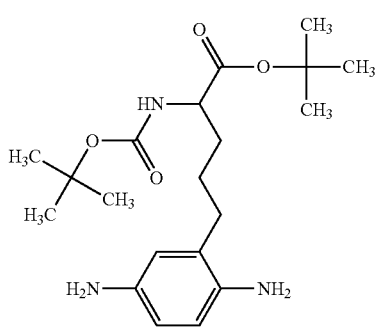

(B)

By reducing a nitro group or an ethylene group of the above-described compound (B6) in accordance with the above-described preparation method of diamine (A), a crude product of the diamine compound of the present invention represented by the above formula (B) can be obtained. The obtained diamine compound is preferably purified by various methods for smooth progression of the polymerization reaction to obtain a polyimide precursor, thereby to obtain a high molecular weight polymer. The purification method may, for example, be silica gel column chromatography or an activated carbon treatment, and is preferably an activated carbon treatment since decomposition of the product is unlikely to occur.

Specific Diamine Compound (C)

The diamine compound of formula (C) may, for example, be prepared via the following 2-steps pathway by using 2-amino-4-nitroaniline of the following formula (C1) and the amino acid derivative of formula (C2) as the main starting materials.

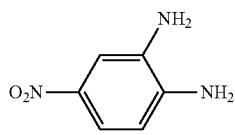

(C1)

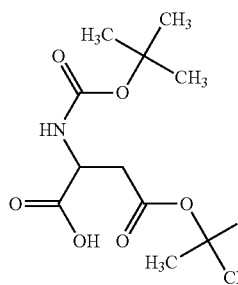

(C2)

Step 1: Preparation of Compound (C3)

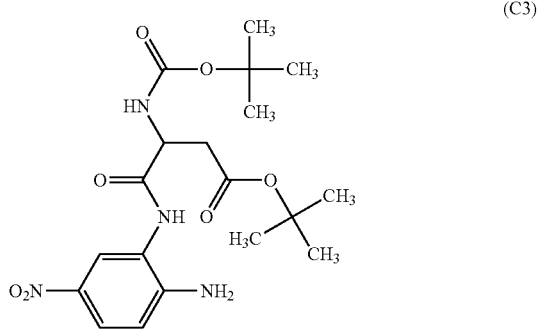

(C3)

The compound of the above formula (C3) can be prepared by condensation reaction of an amino group at the 2-position of 2-amino-4-nitroaniline of the above formula (C1) and a carboxy group of the amino acid derivative of formula (C2).

The nucleophilicity of an amino group at the 1-position of 2-amino-4-nitroaniline decreases due to the effect of a nitro group at the 4-position. Therefore, an amino group at the 2-position and a carboxy group of the amino acid derivative are preferentially react, whereby it becomes possible to prepare compound (C3). If the amino acid derivative is added too much, it forms an amide bond with an amino group at the 4-position, and therefore the amount of the amino acid derivative to be added is preferably from 0.9 to 1.2 times by mole to an amount of 2-amino-4-nitroaniline.

The above-described condensation reaction of an amino group and a carboxy group can be carried out by a known method, and is preferably a method of using a mixed acid anhydride or a method of using a condensing agent.

The method of using a mixed acid anhydride may, for example, be carried out by reacting a carboxylic acid and an acid halide or a chloroformate in an organic solvent in the presence of a base at from −70 to 40° C., preferably from −50 to 5° C., followed by reacting the obtained mixed acid anhydride and an amine compound in an organic solvent at from −70 to 40° C., preferably from −50 to 5° C.

The organic solvent to be used for the reaction is not limited so long as it can dissolve (C2) and does not react with various reagents to be used for the reaction, and is preferably dehydrated chloroform, dichloromethane or tetrahydrofuran, more preferably tetrahydrofuran from the solubility to amino acid derivatives.

The base to be used for the reaction is preferably a tertiary amine, more preferably pyridine, triethylamine, 4-(N,N-dimethylamino)pyridine or N-methylmorpholine. The amount of the base to be added is preferably from 2 to 4 times by mole to the amount of (C1), since if it is too much, the removal tends to be difficult.

The above-described acid halide or chloroformate is preferably pivaloyl chloride, tosyl chloride mesyl chloride, ethyl chloroformate or isobutyl chloroformate. The amount of an acid halide and chloroformate is preferably from 1.1 to 2.0 times by mole to the amount of (C1).

The method of using a condensing agent is carried out by reacting (C1) and (C2) in the presence of a condensing agent, a base and an organic solvent at from 0 to 150° C., preferably from 0 to 100° C., for from 30 minutes to 24 hours, preferably from 3 to 15 hours.

As the above-described condensing agent, triphenylphosphite, dicyclohexylcarbodiimide, 1-ethyl-3-(3-dimethylaminopropyl)carbodiimide hydrochloride, N,N'-carbonyldiimidazole, dimethoxy-1,3,5-triazinylmethylmorpholinium, O-(benzotriazol-1-yl)-N,N,N',N'-tetramethyluronium tetrafluoroborate, O-(benzotriazol-1-yl)-N,N,N',N'-tetramethyluronium hexafluorophosphate or (2,3-dihydro-2-thioxo-3-benzoxazolyl)diphenylphosphonate may, for example, be used. The amount of the condensing agent to be added is preferably from 2 to 3 times by mole to the amount of (C2).

As the above-described base, a tertiary amine such as pyridine or triethylamine may be used. The amount of the base to be added is preferably from 2 to 4 times by mole to the amount of (C1), since if it is too much, the removal tends to be difficult, and if it is too small, the reaction efficiency decreases.

Further, in the above-described method of using a condensing agent, a Lewis acid may be added as an additive to let the reaction proceed efficiently. The Lewis acid is preferably a lithium halide such as lithium chloride or lithium bromide. The amount of the Lewis acid to be added is preferably from 0.1 to 1.0 times by mole to the amount of (C1).

The reaction solution obtained by the above-described two types of methods is preferably subjected to removal of the precipitate, followed by addition of an acidic or basic aqueous solution and an organic solvent to remove an acid halide, chloroformate, a condensing agent, a base and a byproduct derived from these compounds by extraction. The acidic aqueous solution is preferably an aqueous solution of hydrochloric acid, acetic acid, formic acid or ammonium chloride. The basic aqueous solution is preferably an aqueous solution of sodium hydroxide, potassium hydroxide, sodium hydrogencarbonate or potassium carbonate. The organic solvent to be used for the extraction is not limited so long as it does not induce precipitation of the content and is not mixed with water even if it is introduced into the reaction solution, and is preferably ethyl acetate, dichloromethane, chloroform or 1,2-dichloroethane.

The obtained organic phase is subjected to washing several times with the above-described acidic aqueous solution or the above-described basic aqueous solution, followed by drying by a drying agent. The drying agent is preferably sodium sulfate or magnesium sulfate. The drying agent is removed by filtration, and then the solvent is removed by evaporation, thereby to obtain compound (C3). The obtained (C3) can be used for the next reaction without being purified, but is preferably purified by various methods. The purification method may, for example, be silica gel column chromatography, recrystallization and washing with an organic solvent, and is preferably recrystallization from the simplicity of operation and the effectiveness of purification. The organic solvent to be used for the recrystallization is not limited so long as it is an organic solvent which can recrystallize (C3), and two or more types of solvents may be used as mixed for crystallization.

Step 2: Reduction of Compound (C3)

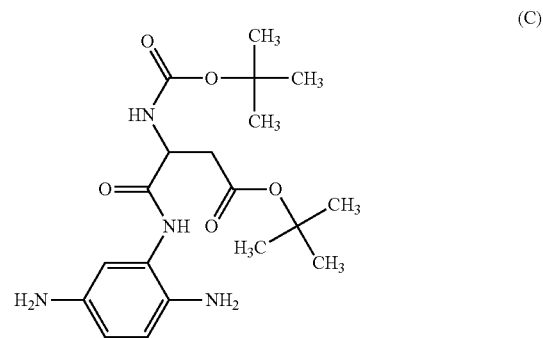

(C)

By reducing a nitro group of the above-described compound (C3) in accordance with the above-described evaporation method of diamine (A), it becomes possible to obtain a crude product of the diamine compound of the present invention represented by the above formula (C). The obtained diamine compound is preferably purified by various methods for smooth progression of the polymerization reaction to obtain a polyimide precursor, thereby to obtain a high molecular weight polymer. The purification method may, for example, be silica gel column chromatography, recrystallization or washing by an organic solvent, and is preferably recrystallization from the simplicity of operation and the effectiveness of purification.

Specific Diamine Compound (D)

The diamine compound of formula (D) may, for example, be prepared by the following method by using t-butyl bromoacetate of the above formula (A2) and p-phenylenediamine of the following formula (D1) as the main starting materials.

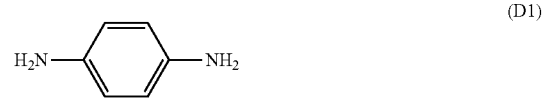

(D1)

Preparation of Diamine (D)

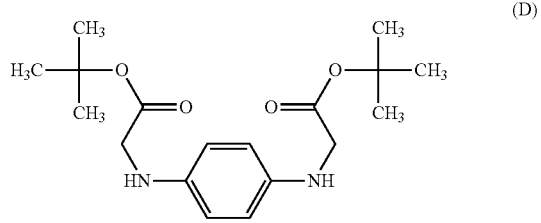 [SMILES: CC(C)(C)OC(=O)CNc1ccc(NCC(=O)OC(C)(C)C)cc1]

p-Phenylenediamine of the above formula (D1) is dissolved in an organic solvent, and then a base is added thereto. Here, the organic solvent to be used is preferably a polar solvent which is commonly used for a nucleophilic substitution reaction, and as specific examples, dimethylformamide, dimethylsulfoxide, acetone and tetrahydrofuran may, for example, be mentioned, but it is not limited thereto. Further, the base may, for example, be potassium hydroxide, sodium hydroxide, potassium carbonate, sodium carbonate, sodium hydrogencarbonate, sodium hydride, triethylamine, diisopropylethylamine, pyridine or 4-(N,N-dimethylamino)pyridine, but it is not limited thereto. Then, the solution is adjusted to a temperature of from −40 to 40° C., preferably from −30 to 30° C., and then while stirring the reaction solution, t-butyl bromoacetate is added in an amount of from 1.0 to 3.0 times by mole, preferably from 1.5 to 2.5 times by mole, to the amount of p-phenylenediamine. At the time of the addition, it is preferably diluted by the same solvent as for the reaction solution, and then dropwise added. Then, the reaction solution is stirred for from 1 to 48 hours, preferably from 2 to 24 hours while maintaining the temperature in a range of from −30 to 30° C., thereby to obtain diamine (D). After completion of the reaction, the solid material in the reaction solution is removed by filtration, and then the filtrate is poured into water to precipitate a crude product of diamine (D). The obtained diamine compound is preferably purified by various methods for smooth progression of the polymerization reaction to obtain a polyimide precursor, thereby to obtain a high molecular weight polymer. The purification method may, for example, be silica gel column chromatography, recrystallization or washing by an organic solvent, and is preferably recrystallization from the simplicity of operation and the effectiveness of purification.

Now, the present invention will be described in further detail with reference to Examples, but it should be understood that the present invention is by no means thereby restricted.

EXAMPLES

Now, measurement methods for $^1$H NMR and molecular weight used for the present examples will be described.
[$^1$H NMR]
Apparatus: Fourier transfer superconducting nuclear magnetic resonance apparatus (FT-NMR) INOVA-400 (manufactured by Varian) 400 MHz
Solvent: Deuterated dimethylsulfoxide (DMSO-$d_6$)
Standard reference material: Tetramethylsilane (TMS)
Cumulated number: 8
[Molecular Weight]
The molecular weight of a polymer was measured by means of a GPC (normal temperature gel permeation chromatography) apparatus, and a number average molecular weight (Mn) and weight average molecular weight (Mw) were calculated as values calculated as polyethylene glycol and polyethylene oxide.
GPC apparatus: Manufactured by Showa Denko K.K. (GPC-101)
Column: Manufactured by Showa Denko K.K. (KD803, KD805 in series)
Temperature of column: 50° C.
Eluent: N,N-dimethylformamide (as additives, 30 mmol/L of lithium bromide monohydrate (LiBr.H$_2$O), 30 mmol/L of phosphoric anhydride crystals (o-phosphoric acid), and 10 mL/L of tetrahydrofuran)
Flow rate: 1.0 mL/min
Standard sample for preparation of a calibration curve: Manufactured by TOSOH CORPORATION, TSK standard polyethylene oxide (weight average molecular weight (Mw): about 900,000, 150,000, 100,000 and 30,000), manufactured by Polymer Laboratory, polyethylene glycol (peak top molecular weight (Mp): about 12,000, 4,000 and 1,000). For the measurement, in order to avoid overlapping of peaks, two samples i.e. a sample having four types of 900,000, 100,000, 12,000 and 1,000 mixed and a sample having three types of 150,000, 30,000 and 4,000 mixed, were separately measured.
<Measurement of Imidation Ratio>
20 mg of a polyimide powder was dissolved in 1 g of deuterated dimethylsulfoxide (mixture of DMSO-$d_6$ and 0.05% TMS (tetramethylsilane)), thereby to measure $^1$H NMR. The imidation ratio was calculated based on the following equation by using a peak derived from a structure which does not change during imidation as a standard, and an integrated value of a peak derived from a NH group of an amide acid found near a range of from 9.5 to 10.0 ppm.

Imidation ratio (%)=(1−α·x/y)×100

In the above equation, x is an integrated value of a peak derived from a NH group of an amide acid, y is an integrated value of a peak for standard, and α is a ratio of the integrated value of a peak derived from a NH group of an amide acid in a polyamide acid (imidation ratio of 0%) to the integrated value of a peak for standard.
<Measurement of Volume Resistivity>
Preparation of an element: a liquid crystal aligning agent was applied on a glass substrate provided with ITO electrodes by spin coating and dried for 5 minutes on a hot plate at 80° C., followed by baking at 230° C. by using an oven with internal air circulation for 60 minutes to obtain a liquid crystal alignment film having a thickness of 200 nm. For some samples, polarized rays with 254 nm were applied on the substrate provided with the liquid crystal alignment film at 1.0 J/cm$^2$. On the prepared substrate provided with a liquid crystal alignment film, aluminum electrodes having a diameter of 1 mm and thickness of 100 nm were formed by vapor deposition to prepare an element for measuring volume resistivity.
Measurement of volume resistivity: In a sealed case connected to electrometer (manufactured by Keithley Instruments Inc., model 617), a voltage of 10 V was applied between the ITO electrodes and aluminum electrodes of the above-described element for 120 seconds, and then the volume resistivity was calculated from an average value of a current flowing from 110 seconds to 120 seconds after application.
Hereinafter, the following abbreviations for compounds may be used.
CBDE-Cl: Dimethyl-1,3-bis(chlorocarbonyl)cyclobutane-2,4-carboxylate
1,3-DMCBDE-Cl: Dimethyl 1,3-bis(chlorocarbonyl)-1,3-dimethylcyclobutane-2,4-carboxylate
TDA: 3,4-Dicarboxy-1,2,3,4-tetrahydro-1-naphthalene-succinic acid dihydride
pPDA: p-Phenylenediamine
TBDA: 1-t-Butoxycarbonyl-3,5-diaminobenzene
EtDA: 1-Ethoxycarbonyl-3,5-diaminobenzene

Example 1

Preparation of Diamine Compound (A)

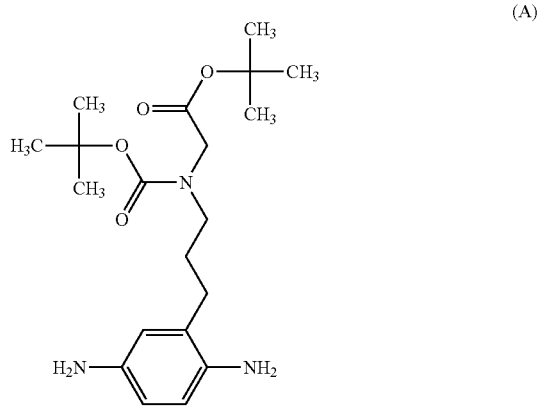 [SMILES: CC(C)(C)OC(=O)CN(CCCc1cc(N)ccc1N)C(=O)OC(C)(C)C]

Diamine compound (A) was prepared by the following 4-steps pathway.

Step 1: Preparation of Compound (A5)

Into a 500 mL eggplant type flask, propargylamine (8.81 g, 160 mmol), N,N-dimethylformamide (112 mL) and potassium carbonate (18.5 g, 134 mmol) were charged in this order, and then adjusted to a temperature of 0° C., followed by dropwise addition of a solution wherein t-butyl bromoacetate (21.9 g, 112 mmol) was dissolved in N,N-dimethylformamide (80 mL) for about 1 hour while stirring. After completion of the dropwise addition, the reaction solution was adjusted to room temperature, and then stirred for 20 hours. Thereafter, the solid material was removed by filtration, and then 1 L of ethyl acetate was added to the filtrate, followed by washing four times with water and once with 300 mL of a saturated sodium chloride aqueous solution. Then, the organic phase was dried by magnesium sulfate, and then the solvent was removed by evaporation under reduced pressure. Finally, the residual oil material was subjected to distillation under reduced pressure under 0.6 Torr at 70° C., thereby to obtain a colorless liquid of t-butyl N-propargylamino acetate (compound (A5)). The total amount of yield was 12.0 g, and the yield rate was 63%.

Step 2: Preparation of Compound (A6)

Into a 1 L eggplant type flask, the above-described t-butyl propargylamino acetate (12.0 g, 70.9 mmol) and dichloromethane (600 mL) were charged to prepare a solution, followed by dropwise addition of a solution wherein di-t-butyl bicarbonate (15.5 g, 70.9 mmol) was dissolved in dichloromethane (100 mL) for 1 hour while stirring with ice-cooling. After completion of the dropwise addition, the reaction solution was adjusted to room temperature, and then stirred for 20 hours. After completion of the reaction, the reaction solution was washed with 300 mL of a saturated sodium chloride aqueous solution, and then dried by magnesium sulfate. Thereafter, the solvent was removed by evaporation under reduced pressure, thereby to obtain a light yellow liquid of t-butyl N-propargylamino-N-t-butoxycarbonyl acetate (compound (A6)). The total amount of yield was 18.0 g, and the yield rate was 94%.

Step 3: Preparation of Compound (A7)

Into a 300 mL four-necked flask, 2-iodo-4-nitroaniline (22.5 g, 85.4 mmol), bis(triphenylphosphine)palladium dichloride (1.20 g, 1.71 mmol), and copper iodide (0.651 g, 3.42 mmol) were charged, and nitrogen substitution was carried out, and then diethylamine (43.7 g, 598 mmol) and N,N-dimethylformamide (128 mL) were added thereto, followed by addition of the above-described t-butyl N-propargylamino-N-t-butoxycarbonyl acetate while stirring with ice-cooling, and further stirring at room temperature for 20 hours. After completion of the reaction, 1 L of ethyl acetate was added thereto, and then washing with 150 mL of a 1 mol/L ammonium chloride aqueous solution was carried out three times and washing with 150 mL of a saturated sodium chloride aqueous solution was carried out once, followed by drying by magnesium sulfate. Thereafter, the solvent was removed by evaporation under reduced pressure to precipitate a solid material, and then the solid material was dissolved in 200 mL of ethyl acetate, followed by addition of 1 L of hexane to carry out recrystallization. The solid material was collected by filtration and dried under reduced pressure, thereby to obtain a yellow solid material of 2-{3-(N-t-butoxycarbonyl-N-t-botxycarbonylmethylamino)-1-propynyl)}-4-nitroaniline (compound (A7)). The total amount of yield was 23.0 g, and the yield rate was 66%.

Step 4: Reduction of Compound (A7)

Into a 500 mL four-necked flask, the above-described 2-{3-(N-t-butoxycarbonyl-N-t-butoxycarbonylmethylamino)-1-propynyl)}-4-nitroaniline (22.0 g, 54.2 mmol) and ethanol (200 g) were charged, and the interior was substituted by nitrogen, and then palladium carbon (2.20 g) was added thereto, followed by hydrogen substitution of the interior and stirring at 50° C. for 48 hours. After completion of the reaction, palladium carbon was removed by Celite filtration, and then activated carbon was added to the filtrate, followed by stirring at 50° C. for 30 minutes. Then, activated carbon was removed by filtration and the organic solvent was removed by evaporation under reduced pressure, and then the residual oil material was dried under reduced pressure, thereby to obtain diamine compound (A). The total amount of yield was 19.8 g, and the yield rate was 96%.

Diamine compound (A) was confirmed by $^1$H NMR.

$^1$H NMR (DMSO-$d_6$): δ 6.54-6.42 (m, 3H, Ar), 3.49, 3.47 (each s, 2H, NCH$_2$CO$_2$t-Bu), 3.38-3.30 (m, 2H, CH$_2$CH$_2$N), 2.51-2.44 (m, 2H, ArCH$_2$), 1.84-1.76 (m, 2H, CH$_2$CH$_2$CH$_2$), 1.48-1.44 (m, 18H, NCO$_2$t-Bu and CH$_2$CO$_2$t-Bu).

Example 2

Preparation of Diamine Compound (B)

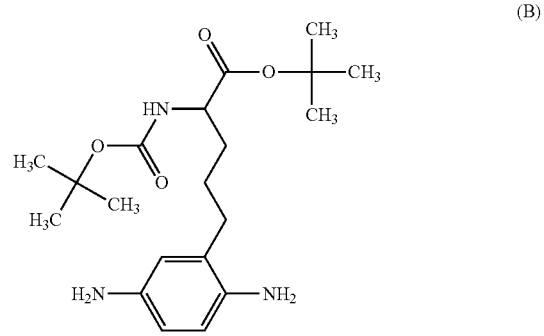 [SMILES: CC(C)(C)OC(=O)NC(CCCc1cc(N)ccc1N)C(=O)OC(C)(C)C]

Diamine compound (B) was prepared by the following 5-steps pathway.

Step 1: Preparation of Compound (B3)

Into a 2 L of eggplant type flask, t-butyl (N-diphenylmethine)glycine (23.6 g, 80.0 mmol), dichloromethane (267 mL), toluene (533 mL), tetrabutylammonium bromide (1.56 g, 4.0 mmol), propargyl bromide (11.4 g, 96.0 mmol) and a 50% potassium hydroxide aqueous solution (157 g) were charged in this order, followed by stirring at room temperature for 20 hours. Then, the organic phase was separated, and the aqueous phase was extracted by ethyl acetate twice. The extract was then combined with the organic phase, followed by washing with 300 mL of a saturated sodium chloride aqueous solution once. Thereafter, the organic phase was dried by magnesium sulfate, and the solvent was removed by evaporation in a reduced pressure, followed by purification of the residual oil material by silica gel column chromatography, thereby to obtain a colorless liquid of t-butyl (N-diphenylmethine)propargylglycine (compound (B3)). The total amount of yield was 26.7 g, and the yield rate was 99%.

Step 2: Preparation of Compound (B4)

Into a 500 mL eggplant type flask, the above-described t-butyl (N-diphenylmethine)propargylglycine (26.7 g, 80.0 mmol), tetrahydrofuran (320 mL) and a wt % citric acid aqueous solution (152 g) were charged, and then stirred at room temperature for 2 hours. After completion of the reaction, 90 mL of 1 mol/L hydrochloric acid was added, the aqueous phase was separated, and then washing by 160 mL of ethyl acetate was carried out three times, followed by addition of potassium carbonate until the pH became 8. Thereafter, the aqueous phase was extracted by 160 mL of ethyl acetate three times, and the extract was then combined with the organic phase, followed by drying by magnesium sulfate. Finally, the solvent was removed by evaporation under reduced pressure, and then the residual oil material was dried under reduced pressure, thereby to obtain a yellow liquid of t-butyl propargylglycine (compound (B4)). The total amount of yield was 8.51 g, and the yield rate was 63%.

Step 3: Preparation of Compound (B5)

Into a 1 L eggplant type flask, the above-described t-butyl propargylglycine (6.43 g, 38.0 mmol), dichloromethane (127 mL), triethylamine (4.23 g, 41.2 mmol) and di-t-butyl bicarbonate (9.12 g, 41.2 mmol) were charged in this order, and then stirred at room temperature for 20 hours. After completion of the reaction, the reaction solution was washed with 100 mL of a saturated sodium chloride aqueous solution, and then dried by magnesium sulfate. Then, the solvent was removed by evaporation under reduced pressure, thereby to obtain an orange colored liquid of t-butyl N-t-butoxycarbonylpropargylglycine (compound (B5)). The total amount of yield was 9.69 g, and the yield rate was 95%.

Step 4: Preparation of Compound (B6)

Into a 200 mL four-necked flask, 2-iodo-4-nitroaniline (8.72 g, 33.0 mmol), bis(triphenylphosphine)palladium dichloride (0.463 g, 0.660 mmol) and copper iodide (0.251 g, 1.32 mmol) were charged, and nitrogen substitution was carried out, and then diethylamine (16.9 g, 231 mmol) and N,N-dimethylformamide (50 mL) were added thereto. While stirring with ice-cooling, the above-described t-butyl N-t-butoxycalpropargylglycine (9.69 g, 36.0 mmol) dissolved in N,N-dimethylformamide (16 mL) was added, followed by stirring at room temperature for 16 hours. After completion of the reaction, 500 mL of ethyl acetate was added, and then washing with 100 mL of a 1 mol/L ammonium chloride aqueous solution was carried out three times and washing with 100 mL of a saturated sodium chloride aqueous solution was carried out once, followed by drying by magnesium sulfate. Then, the solvent was removed by evaporation under reduced pressure and the residual oil material was purified by silica gel column chromatography, thereby to obtain a yellow solid of 2-{4-(N-t-butoxycarbonylamino)-4-(t-butoxycarbonyl)-1-butynyl}-4-nitroaniline (compound (B6)). The total amount of yield was 5.54 g, and the yield rate was 41%.

Step 5: Reduction of Compound (B6)

Into a 500 mL four-necked flask, the above-described 2-{4-(N-t-butoxycarbonylamino)-4-(t-butoxycarbonyl)-1-butynyl}-4-nitroaniline (5.54 g, 13.7 mmol) and ethanol (49.9 g) were charged, and the interior was substituted with nitrogen, and then palladium carbon (0.540 g) was added thereto. Thereafter, the interior was substituted with hydrogen, followed by stirring at 50° C. for 48 hours. After completion of the reaction, palladium carbon was removed by Celite filtration, and then activated carbon was added to the filtrate, followed by stirring at 50° C. for 30 minutes. Then, activated carbon was removed by filtration, the organic solvent was removed by evaporation under reduced pressure, and then the formed oil material was dried under reduced pressure, thereby to obtain diamine compound (B). The total amount of yield was 3.90 g, and the yield rate was 85%.

The structure of diamine compound (B) was confirmed by $^1$H NMR.

$^1$H NMR (DMSO-$d_6$): δ 7.15 (d, J=7.6 Hz, 1H, Ar), 6.37 (d, J=8.0 Hz, 1H, Ar), 6.24-6.20 (dd, J=8.0, 7.6 Hz, 1H, Ar), 4.09 (br s, 4H, NH$_2$), 3.79 (m, 1H, NCH), 2.27 (m, 2H, ArCH$_2$), 1.72-145 (m, 4H, —CH$_2$CH$_2$—), 1.38 (s, 18H, t-Bu).

Example 3

Preparation of Diamine Compound (C)

Diamine compound (C) was prepared by the following 2-steps pathway.

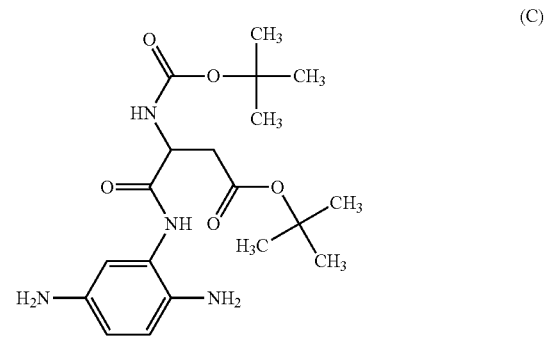 [SMILES: CC(C)(C)OC(=O)CC(NC(=O)OC(C)(C)C)C(=O)Nc1cc(N)ccc1N]

Step 1: Preparation of Compound (C3)

Into a 500 mL four-necked flask charged with nitrogen, amino acid derivatives (5.00 g, 17.3 mmol) was introduced and then dissolved in THF (tetrahydrofuran) (150 mL). Then, NMM (N-methylmorpholine) (3.55 g, 35.1 mmol) was added thereto, followed by cooling to a temperature of −45° C. Into this solution, isobutyl chloroformate (2.97 g, 21.8 mmol) was added, followed by stirring at −45° C. for 10 minutes. Upon expiration of 10 minutes, a solution prepared by dissolving 2-amino-4-nitroaniline (2.59 g, 16.9 mmol) to THF (100 mL) was dropwise added. After completion of the dropwise addition, stirring was carried out for 1 hour at −45° C., and then further stirring was carried out for 18 hours at 20° C. After completion of the reaction, the precipitated solid material was removed by filtration, and then the obtained filtrate was concentrated under reduced pressure. The residue was dissolved in 500 mL of ethyl acetate and 500 mL of THF, followed by washing with 200 mL of a potassium dihydrogenphosphate aqueous solution (1 mol/L) twice, washing with 200 mL of a saturated sodium chloride aqueous solution once, washing with 200 mL of a saturated sodium hydrogencarbonate aqueous solution two times, and then washing with 200 mL of a saturated sodium chloride aqueous solution once finally. The obtained organic phase was dried by magnesium sulfate, and the solvent was removed by evaporation under reduced pressure, followed by washing the residual light yellow solid material with ethyl acetate, thereby to obtain 2-(3-t-butoxycarbonyl-2-t-butoxrarbonylaminopropionylamino)-4-nitroaniline (compound (C3)). The total amount of yield was 4.88 g, and the yield rate was 68.0%.

Step 2: Reduction of Compound (C3)

Into a 300 mL eggplant type flask, compound (C3) (4.85 g, 11.4 mmol) was introduced and then ethanol (150 mL) was charged, and then the interior was substituted with nitrogen. Thereafter, palladium carbon (0.49 g) was added, and then the interior was substituted with hydrogen, followed by stirring at 20° C. for 48 hours. After completion of the reaction, the precipitate was removed by Celite filtration, and then the solvent was removed by evaporation under reduced pressure. The obtained residual oil material was recrystallized by using toluene, thereby to obtain a light purple colored solid material of diamine compound (C). The total amount of yield was 3.03 g, and the yield rate was 67%.

The structure of diamine compound (C) was confirmed by $^1$H NMR.

$^1$H NMR (DMSO-$d_6$): δ 8.99 (s, 1H, NHCO$_2$t-Bu), 7.20 (d, J=8.0 Hz, 1H, ArNH), 6.59 (d, J=2.8 Hz, Ar), 6.49 (d, J=8.0 Hz, 2H, Ar), 6.24 (dd, J=8.0, 2.8 Hz, 1H, Ar), 4.23 (dd, J=8.8, 4.7 Hz, 1H, CH), 4.35, 4.00 (each s, 4H, NH$_2$), 2.72 (dd, J=16.0, 4.7 Hz, 1H, CH$_2$), 2.49 (dd, J=16.0, 8.8 Hz, 1H, CH$_2$), 1.40 (s, 18H, t-Bu).

Example 4

Preparation of Diamine Compound (D)

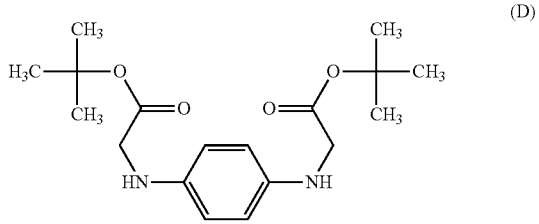 [SMILES: CC(C)(C)OC(=O)CNc1ccc(NCC(=O)OC(C)(C)C)cc1]

Into a 500 mL eggplant type flask, p-phenylenediamine (16.2 g, 150 mmol), N,N-dimethylformamide (200 mL) and potassium carbonate (49.8 g, 360 mmol) were charged, and then the mixture was cooled to −20° C. Then, a solution prepared by dissolving t-butyl boromoacetate (58.5 g, 300 mmol) to N,N-dimethylformamide (100 mL) was dropwise added thereto for 3 hours. Thereafter, stirring was carried out at room temperature for 20 hours. After removal of the solid material in the reaction solution by filtration, the filtrate was poured into 6 L of water, thereby to collect a crude product of the precipitated diamine compound (D). The obtained crude product was dissolved in 100 mL of DMF, and then poured into 2 L of water again to precipitate a solid material. The solid material was washed with methanol and then dried under reduced pressure, thereby to obtain a light pink colored solid material of diamine compound (D). The total amount of yield was 25.1 g, and the yield rate was 50%.

The structure of diamine compound (D) was confirmed by $^1$H NMR.

$^1$H NMR (DMSO-$d_6$): δ 6.39 (s, 4H, Ar), 5.09 (t, J=6.6 Hz, 2H, NH), 3.64 (d, J=6.6 Hz, 4H, CH$_2$), 1.39 (s, 18H, t-Bu).

Example 5

Preparation of Polyimide Precursor

Into a 300 mL four-necked flask, p-phenylenediamine (0.700 g, 6.47 mmol) and diamine compound (D) (0.191 g, 0.719 mmol) were charged, and then NMP (N-methyl-2-pyrrolidone) (44.6 mL) and pyridine (1.39 mL, 17.3 mmol) were added to dissolve them. Then, while stirring this solution with water-cooling, CBDE-Cl (dimethyl-1,3-bis(chlorocarbonyl)cyclobutane-2,4-carboxylate) (2.14 g, 7.19 mmol) was added thereto, and further NMP was added so that the solid content concentration would be 5 mass %, followed by stirring for 4 hours with ice-cooling. The solution was poured into 250 g of water to precipitate a polymer, and then the polymer was collected by suction filtration, followed by washing with 250 g of water again, washing with methanol (63 g×3 times), and drying under reduced pressure at 40° C., thereby to obtain a powder of polyamic acid ester [A]. The molecular weight of this polyamic acid ester was Mn=12,652 and Mw=27,434.

Example 6

Preparation of Polyimide Precursor

Into a 50 mL four-necked flask, diamine compound (A) (0.530 g, 1.40 mmol) and p-phenylenediamine (0.604 g, 5.59 mmol) were charged, and then NMP (9.8 mL), γ-BL (γ-butyrolactone) (13.1 mL) and pyridine (1.31 mL, 16.3 mmol) were added and dissolved. Then, while stirring this solution with water-cooling, CBDE-Cl (2.01 g, 6.77 mmol) was added thereto, and further NMP was added so that the solid content concentration would be 8 mass %, followed by stirring for 4 hours with water-cooling. Thereafter, a mixed solution having a NMP:γ-BL weight ratio of 1:1 was added so that the solid content concentration would be 5 mass %, followed by pouring into 265 g of water to precipitate a polymer, and then the polymer was collected by suction filtration, followed by washing with 265 g of water again and washing with ethanol (once with 265 g, and three times with 65 g). Thereafter, drying under reduced pressure was carried out at 40° C. for 3 hours and then at 60° C. for 5 hours, thereby to obtain a powder of polyamic acid ester [B]. Further, the molecular weight of this polyamic acid ester was Mn=25,934 and Mw=78,562.

Comparative Example 1

Preparation of Polyimide Precursor

Into a 50 mL two-necked flask, p-phenylenediamine (0.700 g, 6.47 mmol) was charged, and NMP (21.7 mL) and pyridine (1.56 mL, 19.4 mmol) were added and dissolved. While stirring this solution with water-cooling, CBDE-Cl (1.92 g, 6.47 mmol) was added thereto, and further NMP was added so that the solid content concentration would 8 mass %, followed by stirring for 1 hour with water-cooling. Then, NMP was added to this solution so that the solid content concentration would be 5 mass %, and then the solution was poured into 215 g of water to precipitate a polymer. Then, the polymer was collected by suction filtration, and then washed again with 215 g of water and methanol (three times with 54 g), followed by drying under reduced pressure at 40° C., thereby to obtain a powder of polyamic acid ester [C]. Further, the molecular weight of polyamic acid water Mn=24,559 and Mw=73,634.

Example 7

Preparation of Polyimide Precursor

Into a 3 L three-necked flask, diamine compound (A) (43.6 g, 115 mmol) and p-phenylenediamine (44.0 g, 407 mmol) were charged, and then NMP (820 mL), γ-BL (623 mL) and pyridine (93.4 mL) were added and dissolved. While stirring this solution with water-cooling, 1,3-DMCBDE-Cl (dimethyl 1,3-bis(chlorocarbonyl)-1,3-dimethylcyclobutane-2,4-carboxylate) (158 g, 486 mmol) was added thereto, and further NMP was added so that the solid content concentration would be 10 mass %, followed by stirring for 4 hours with water-cooling. A mixed solvent having a NMP:γ-BL weight ratio of 1:1 was added so that the solid content concentration would be 5 mass %, and then the solution was poured into 2.10 kg of water to precipitate a polymer. Then, the polymer was collected by suction filtration, and then washed again with 2.10 kg of water and then washed with ethanol (once with 2.10 kg, and three times with 525 g), followed by drying under reduced pressure at 40° C. for 3 hours and then at 60° C. for 5 hours, thereby to obtain a powder of polyamic acid ester [D]. Further, the molecular weight of this polyamic acid ester was Mn=13,350 and Mw=28,323.

Example 8

Preparation of Polyimide Precursor

Into a 500 mL three-necked flask, diamine compound (A) (3.35 g, 8.82 mmol) and p-phenylenediamine (0.953 g, 8.81 mmol) were introduced, and then NMP (156 mL) and pyridine (3.40 mL) were added and dissolved. While stirring this solution with water-cooling, 1,3-DMCBDE-Cl (5.73 g, 17.6 mmol) was added thereto, and further NMP was added so that the solid content concentration would be 5 mass %, followed by stirring for 4 hours with water-cooling. Then this solution was poured into 875 g of water to precipitate a polymer, and then the polymer was collected by suction filtration, followed by washing with 875 g of water again, washing with ethanol (once with 875 g, and three times with 219 g), and drying under reduced pressure at 40° C. for 3 hours and then at 60° C. for 5 hours, thereby to obtain a powder of polyamic acid ester [E]. Further, the molecular weight of this polyamic acid ester was Mn=30,549 and Mw=57,127.

Example 9

Preparation of Polyimide Precursor

Into a 50 mL three-necked flask, diamine compound (B) (1.14 g, 3.00 mmol) and p-phenylenediamine (0.235 g, 3.00 mmol) were charged, and then NMP (6.8 mL) and pyridine (1.2 mL) were added and dissolved. While stirring this solution with water-cooling, 1,3-DMCBDE-Cl (1.95 g, 6.01 mmol) was added thereto, and further NMP was added so that the solid content concentration would be 10 mass %, followed by stirring for 4 hours with water-cooling. Then, this solution was poured into 298 g of water to precipitate a polymer, and then the polymer was collected by suction filtration, followed by washing with 298 g of water again, washing with ethanol (once with 298 g, and three times with 75 g), and drying under reduced pressure at 40° C. for 3 hours and then at 60° C. for 5 hours, thereby to obtain a powder of polyamic acid ester [F]. Further, the molecular weight of this polyamic acid ester was Mn=26,518 and Mw=47,398.

Example 10

Preparation of Polyimide Precursor

Into a 300 mL three-necked flask, diamine compound (C) (0.502 g, 1.27 mmol) and p-phenylenediamine (0.550 g, 5.09 mmol) were charged, and then NMP (47.4 mL) and pyridine (1.23 mL) were added and dissolved. While stirring this solution with water-cooling, 1,3-DMCBDE-Cl (2.07 g, 6.36 mmol) was added thereto, and further NMP was added so that the solid content concentration would be 5 mass %, followed by stirring for 4 hours with water-cooling. Then, this solution was poured into 266 g of water to precipitate a polymer, and then the polymer was collected by suction filtration, followed by washing with 266 g of water again, washing with ethanol (once with 266 g, and three times with 66 g), and drying under reduced pressure at 40° C. for 3 hours and then at 60° C. for 5 hours, thereby to obtain a powder of polyamic acid ester [G]. Further, the molecular weight of this polyamic acid ester was Mn=48,729 and Mw=94,484.

Example 11

Preparation of Polyimide Precursor

Into a 50 mL three-necked flask, diamine compound (D) (0.277 g, 0.822 mmol) and p-phenylenediamine (0.800 g, 7.40 mmol) were charged, and then NMP (56.8 mL) and pyridine (1.59 mL) were added and dissolved. While stirring this solution with water-cooling, 1,3-DMCBDE-Cl (2.67 g, 8.22 mmol) was added thereto, and further NMP was added so that the solid content concentration would be 5 mass %, followed by stirring for 4 hours with water-cooling. Then, this solution was poured into 315 g of water to precipitate a polymer, and then the polymer was collected by suction filtration, followed by washing with 315 g of water again, washing with methanol (five times with 79 g), and drying under reduced pressure at 40° C. for 5 hours, thereby to obtain a powder of polyamic acid ester [H]. Further, the molecular weight of this polyamic acid ester was Mn=12,994 and Mw=23,104.

Comparative Example 2

Preparation of Polyimide Precursor

Into a 1 L three-necked flask, p-phenylenediamine (6.99 g, 64.6 mmol) was charged, and then NMP (386 mL) and pyridine (11.9 mL) were added and dissolved. While stirring this solution with water-cooling, 1,3-DMCBDE-Cl (20.0 g, 61.4 mmol) was added thereto, and further NMP was added so that the solid content concentration would be 5 mass %, followed by stirring for 4 hours with water-cooling. Then, this solution was poured into 2.24 kg of water to precipitate a polymer, and then the polymer was collected by suction filtration, followed by washing with 2.24 kg of water again, washing with ethanol (once with 2.24 kg, and three times with 562 g), and drying under reduced pressure at 40° C. for 3 hours and then at 60° C. for 5 hours, thereby to obtain a powder of polyamic acid ester

[I]. Further, the molecular weight of this polyamic acid ester was Mn=16,813 and Mw=38,585.

Example 12

Preparation of Polyimide Precursor

Into a 50 mL four-necked flask, TBDA (1-t-butoxycarbonyl-3,5-diaminobenzene, 1.46 g, 7.01 mmol) was charged, and then NMP (14.3 g) was added and dissolved. To this solution, TDA (3,4-dicarboxy-1,2,3,4-tetrahydro-1-naphthalenesuccinic acid dianhydride) (2.10 g, 6.99 mmol) was added, followed by stirring in an oil bath maintained at 40° C. for 90 hours, thereby to obtain a solution of polyamic acid [J]. Further, the molecular weight of this polyamic acid was Mn=11,074 and Mw=26,449.

Example 13

Preparation of Polyimide

Into a 50 mL Erlenmeyer flask, a solution of polyamic acid (4.96 g) obtained in Example 4 was charged, and then NMP was added so that the solid content concentration would be 6 mass %. Then, acetic anhydride (2.39 g) and pyridine (1.11 g) were added thereto, followed by stirring at room temperature for 30 minutes and then at 40° C. for 3 hours. This solution was poured into 81.9 g of methanol to precipitate a polymer, and then the polymer was collected by suction filtration, followed by washing with methanol (two times with 23.4 g) again and drying under reduced pressure at 100° C., thereby to obtain a powder of polyimide [K]. Further, the molecular weight of this polyimide was Mn=10,317 and Mw=23,312. Further, the imidation ratio calculated from $^1$H NMR was 89%.

Comparative Example 3

Preparation of Polyimide Precursor

Into a 50 mL four-necked flask, EtDA (1-ethoxycarbonyl-3,5-diaminobenzene, 2.69 g, 14.9 mmol) was charged, and then NMP (28.7 g) was added and dissolved. To this solution, TDA (4.45 g, 14.8 mmol) was added, followed by stirring at 40° C. in an oil bath for 27 hours, thereby to obtain a solution of polyamic acid [L]. Further, the molecular weight of this polyamic acid was Mn=7,611 and Mw=14,341.

Comparative Example 4

Preparation of Polyimide

Into a 50 mL Erlenmeyer flask, a solution of polyamic acid (10.0 g) obtained in Comparative Example 5 was charged, and then NMP was added so that the solid content concentration would be 6 mass %. Then, acetic anhydride (4.70 g) and pyridine (2.18 g) were added thereto, followed by stirring at room temperature for 30 minutes and then at 40° C. for 3 hours. This solution was poured into 153 g of methanol to precipitate a polymer, and then the polymer was collected by suction filtration, followed by washing with methanol (two times with 43.7 g) again and drying under reduced pressure at 100° C., thereby to obtain a powder of polyimide [M]. Further, the molecular weight of this polyimide was Mn=7,748 and Mw=14,307. Further, the imidation ratio calculated from $^1$H NMR was 94%.

Example 14

Preparation of Polyimide Precursor Varnish 0.204 g of the powder of polyamic acid ester [B] was dissolved in NMP (3.95 g), and then BS (butylcellosolve) (1.0 g) was added to this solution, thereby to prepare a 4 mass % polyamic acid ester varnish [B-1].

Comparative Example 5

Preparation of Polyimide Precursor Varnish 0.199 g of the powder of polyamic acid ester [α] was dissolved in DMF (N,N-dimethylformamide) (1.81 g), and then NMP (2.00 g) and BS (butylcellosolve) (1.01 g) were added to this solution, thereby to prepare a 4 mass % polyamic acid ester varnish [C-1].

Example 15

Preparation of Polyimide Precursor Varnish 0.602 g of the powder of polyamic acid ester [D] was dissolved in γ-BL (5.41 g), and then γ-BL (2.00 g) and BS (1.99 g) were added to this solution, thereby to prepare a 6 mass % polyamic acid ester vanish [D-1].

Example 16

Preparation of Polyimide Precursor Varnish 0.302 g of the powder of polyamic acid ester [E] was dissolved in γ-BL (2.72 g), and then γ-BL (1.00 g) and BS (1.00 g) were added to this solution, thereby to prepare a 6 mass % polyamic acid ester vanish [E-1].

Example 17

Preparation of Polyimide Precursor Varnish 0.301 g of the powder of polyamic acid ester [F] was dissolved in γ-BL (2.70 g), and then γ-BL (1.00 g) and BS (1.00 g) were added to this solution, thereby to prepare a 6 mass % polyamic acid ester vanish [F-1].

Example 18

Preparation of Polyimide Precursor Varnish 0.308 g of the powder of polyamic acid ester [G] was dissolved in γ-BL (2.73 g), and then γ-BL (1.00 g) and BS (1.00 g) were added to this solution, thereby to prepare a 6 mass % polyamic acid ester vanish [G-1].

Example 19

Preparation of Polyimide Precursor Varnish 0.603 g of the powder of polyamic acid ester [H] was dissolved in DMF (N,N-dimethylformamide) (5.42 g), and then NMP (1.99 g) and BS (2.07 g) were added to this solution, thereby to prepare a 6 mass % polyamic acid ester varnish [H-1].

Comparative Example 6

Preparation of Polyimide Precursor Varnish 0.631 g of the powder of polyamic acid ester [I] was dissolved in DMF (5.67 g), and then γ-BL (2.13 g) and BS (2.10 g) were added to this solution, thereby to prepare a 6 mass % polyamic acid ester varnish [I-1].

Example 20

Preparation of Polyimide Precursor Varnish

Into 1.82 g of the solution of polyamic acid [J], NMP (2.18 g) was dissolved and then NMP (1.99 g) and BS (1.00 g) were added to this solution, thereby to prepare a 8 mass % polyamic acid varnish [J-1].

Example 22

Preparation of Polyimide Varnish 0.604 g of the powder of polyimide [K] was dissolved in γ-BL (5.40 g), and then γ-BL (2.10 g) and BS (2.03 g) were added to this solution, thereby to prepare a 6 mass % polyimide varnish [K-1].

Comparative Example 7

Preparation of Polyimide Precursor Varnish

Into 1.82 g of the solution of polyamic acid [L], NMP (2.18 g) was dissolved, and then NMP (1.99 g) and BS (1.00 g) were added to this solution, thereby to prepare a 8 mass % polyamic acid varnish [L-1].

Comparative Example 8

Preparation of Polyimide Varnish 0.601 g of the powder of polyimide [M] was dissolved in γ-BL (5.40 g), and then γ-BL (2.01) and BS (2.03 g) were added to this solution, thereby to prepare a 6 mass % polyimide varnish [M-1].

Examples 23 to 31, and Comparative Examples 9 to 13

Measurement of Volume Resistivity

The volume resistivities of the above-prepared vanishes were measured. With regard to varnishes [B-1] and [C-1], the volume resistivities after application of polarized ultraviolet rays with 254 nm were also measured. Results are shown in Table 1.

Example 32

The liquid crystal aligning agent (B-1) obtained in Example 14 was filtrated by a filter of 1.0 μm, then applied on a glass substrate provided with transparent electrodes by spin coating and dried for 5 minutes on a hot plate at a temperature of 80° C., followed by baking at 230° C. for 20 minutes to obtain a polyimide film having a thickness of 100 nm. On this coating film substrate, ultraviolet rays with 254 nm were applied at a 1.0 J/cm² via a polarizer to obtain a substrate provided with a liquid crystal alignment film. Two such substrates each provided with a liquid crystal alignment film were prepared, and on the liquid crystal alignment film surface of one of the substrates, a spacer of 6 μm was scattered. Then, the two substrates were combined so that the alignment directions of the two substrates were twisted by 85° from the parallel direction, and except for a liquid crystal injection inlet, the periphery was sealed to prepare a vacant cell with a cell gap of 6 μm. To this vacant cell, liquid crystal (MLC-2003, manufactured by Merck) was vacuum-injected at room temperature, and the injection inlet was sealed to obtain a twist nematic liquid crystal cell. The alignment state of this liquid crystal cell was observed by a polarizing microscope, whereby uniform alignment free from defects was confirmed.

TABLE 1

|  | Liquid crystal aligning agent | Acid dianhydride/ acid dichloride | Diamine | Polarized rays | Volume resistivity [Ω · cm] |
|---|---|---|---|---|---|
| Ex. 23 | B-1 | CBDE-Cl | pPDA(80), A(20) | Not applied | $1 \times 10^{12}$ |
| Comp. Ex. 9 | C-1 | CBDE-Cl | pPDA | Not applied | $3 \times 10^{13}$ |
| Ex. 24 | D-1 | 1,3-DMCBDE-Cl | pPDA(80), A(20) | Not applied | $3 \times 10^{13}$ |
| Ex. 25 | E-1 | 1,3-DMCBDE-Cl | pPDA(50), A(50) | Not applied | $5 \times 10^{12}$ |
| Ex. 26 | F-1 | 1,3-DMCBDE-Cl | pPDA(80), B(20) | Not applied | $3 \times 10^{13}$ |
| Ex. 27 | G-1 | 1,3-DMCBDE-Cl | pPDA(80), C(20) | Not applied | $3 \times 10^{13}$ |
| Ex. 28 | H-1 | 1,3-DMCBDE-Cl | pPDA(90), D(10) | Not applied | $4 \times 10^{13}$ |
| Comp. Ex. 10 | I-1 | 1,3-DMCBDE-Cl | pPDA | Not applied | $7 \times 10^{13}$ |
| Ex. 29 | J-1 | TDA | TBDA | Not applied | $7 \times 10^{13}$ |
| Ex. 30 | K-1 | TDA | TBDA | Not applied | $4 \times 10^{12}$ |
| Comp. Ex. 11 | L-1 | TDA | EtDA | Not applied | $1 \times 10^{15}$ |
| Comp. Ex. 12 | M-1 | TDA | EtDA | Not applied | $3 \times 10^{15}$ |
| Ex. 31 | B-1 | CBDE-Cl | pPDA(80), A(20) | Applied | $1 \times 10^{14}$ |
| Comp. Ex. 13 | C-1 | CBDE-Cl | pPDA | Applied | $5 \times 10^{14}$ |

In Table 1, the figures in parentheses indicate mol % of two types of diamines.

INDUSTRIAL APPLICABILITY

The liquid crystal aligning agent of the present invention becomes a liquid crystal alignment film suitable for preparing a liquid crystal display element having an excellent DC characteristics, when it is used as a liquid crystal alignment film of a liquid crystal display element.

The polyimide precursor and polyimide of the present invention can provide a polyimide film having a low volume resistivity.

The diamine compound of the present invention is the best starting material for obtaining the polyimide precursor and polyimide of the present invention, and the liquid crystal alignment film prepared therefrom.

The entire disclosure of Japanese Patent Application No. 2009-056426 filed on Mar. 10, 2009 including specification, claims and summary is incorporated herein by reference in its entirety.

The invention claimed is:

1. A diamine compound represented by any one of the following formulae (A) to (C):

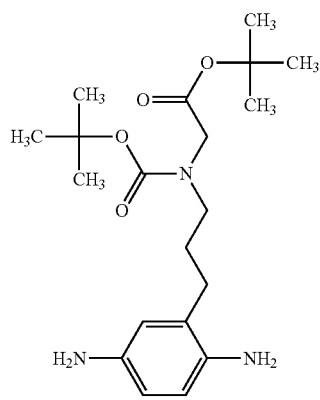

(A)

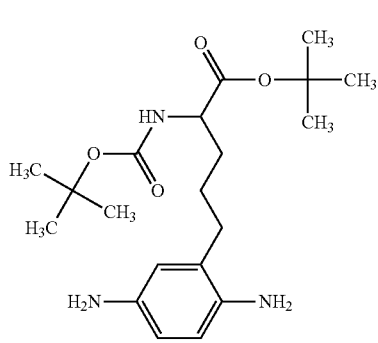

(B)

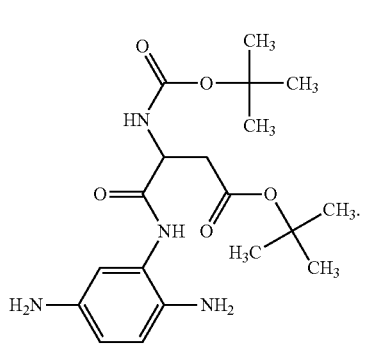

(C)

* * * * *